(12) United States Patent
Llop et al.

(10) Patent No.: US 8,899,984 B2
(45) Date of Patent: Dec. 2, 2014

(54) CT-BASED, SIDE-LOADING SURGICAL AND LABORATORY DENTAL IMPLANT GUIDE SYSTEM AND METHOD

(76) Inventors: Daniel R. Llop, Reno, NV (US); Brad J. Hawley, Grass Valley, CA (US)

(*) Notice: Subject to any disclaimer, the term of this patent is extended or adjusted under 35 U.S.C. 154(b) by 70 days.

(21) Appl. No.: 12/683,319

(22) Filed: Jan. 6, 2010

(65) Prior Publication Data

US 2010/0297574 A1      Nov. 25, 2010

Related U.S. Application Data

(60) Provisional application No. 61/216,711, filed on May 20, 2009.

(51) Int. Cl.
| | |
|---|---|
| *A61C 19/04* | (2006.01) |
| *A61C 8/02* | (2006.01) |
| *A61C 8/00* | (2006.01) |
| *A61C 1/08* | (2006.01) |
| *A61C 3/02* | (2006.01) |

(52) U.S. Cl.
CPC .............. *A61C 8/0089* (2013.01); *A61C 8/0006* (2013.01); *A61C 1/084* (2013.01); *A61C 3/02* (2013.01); *A61C 8/0022* (2013.01); *A61C 8/0018* (2013.01)
USPC .............................................. 433/215; 433/72

(58) Field of Classification Search
USPC .......................... 433/39, 136–138, 51, 72–76; 606/96–99
See application file for complete search history.

(56) References Cited

U.S. PATENT DOCUMENTS

| | | | | |
|---|---|---|---|---|
| 5,007,836 | A * | 4/1991 | Gayso ........................ | 433/181 |
| 5,320,529 | A * | 6/1994 | Pompa ....................... | 433/76 |
| 5,704,788 | A * | 1/1998 | Milne ......................... | 433/173 |
| 5,797,741 | A * | 8/1998 | Bonpard et al. ........... | 433/75 |
| 5,967,777 | A * | 10/1999 | Klein et al. ................. | 433/75 |
| 6,000,939 | A * | 12/1999 | Ray et al. ................... | 433/27 |
| 6,626,911 | B1 * | 9/2003 | Engman et al. ............ | 606/916 |
| 6,644,969 | B2 * | 11/2003 | Kumar ........................ | 433/173 |
| 2002/0169439 | A1 * | 11/2002 | Flaherty ..................... | 604/891.1 |
| 2005/0287492 | A1 * | 12/2005 | Lazzarato ................... | 433/72 |

(Continued)

FOREIGN PATENT DOCUMENTS

WO    WO 2005120385 A1 * 12/2005 ............... A61C 8/00

OTHER PUBLICATIONS

English translation of WO 2005120385 A1.*

(Continued)

*Primary Examiner* — Chris L Rodriguez
*Assistant Examiner* — Matthew Seward
(74) *Attorney, Agent, or Firm* — Long & Chybik; John D. Long, Esq.

(57) ABSTRACT

One possible embodiment of the invention could be a dental surgical guide and a methodology of operating same, the dental surgical guide having a body with a set of walls, a top portion, and a bottom portion and at least one open-sided channel, the open-sided channel continuously connects an opening of the one of the set of walls to the top portion and the bottom portion; and at least one master grommet, the master grommet having a hollow grommet interior that continuously connects a side opening, a top aperture and a bottom aperture; wherein the open-sided master grommet is placed within a respective open-sided channel to allow a dental tooling head to be placed into the master grommet through the master grommet's side opening.

31 Claims, 18 Drawing Sheets

(56) References Cited

U.S. PATENT DOCUMENTS

2006/0257817 A1* 11/2006 Shelton ............................ 433/75
2007/0298373 A1* 12/2007 Lette et al. ...................... 433/72
2008/0153060 A1   6/2008 DeMoyer

OTHER PUBLICATIONS

PCT International Search Report for Daniel R. Llop et al, PCT/US2010/035545.

* cited by examiner

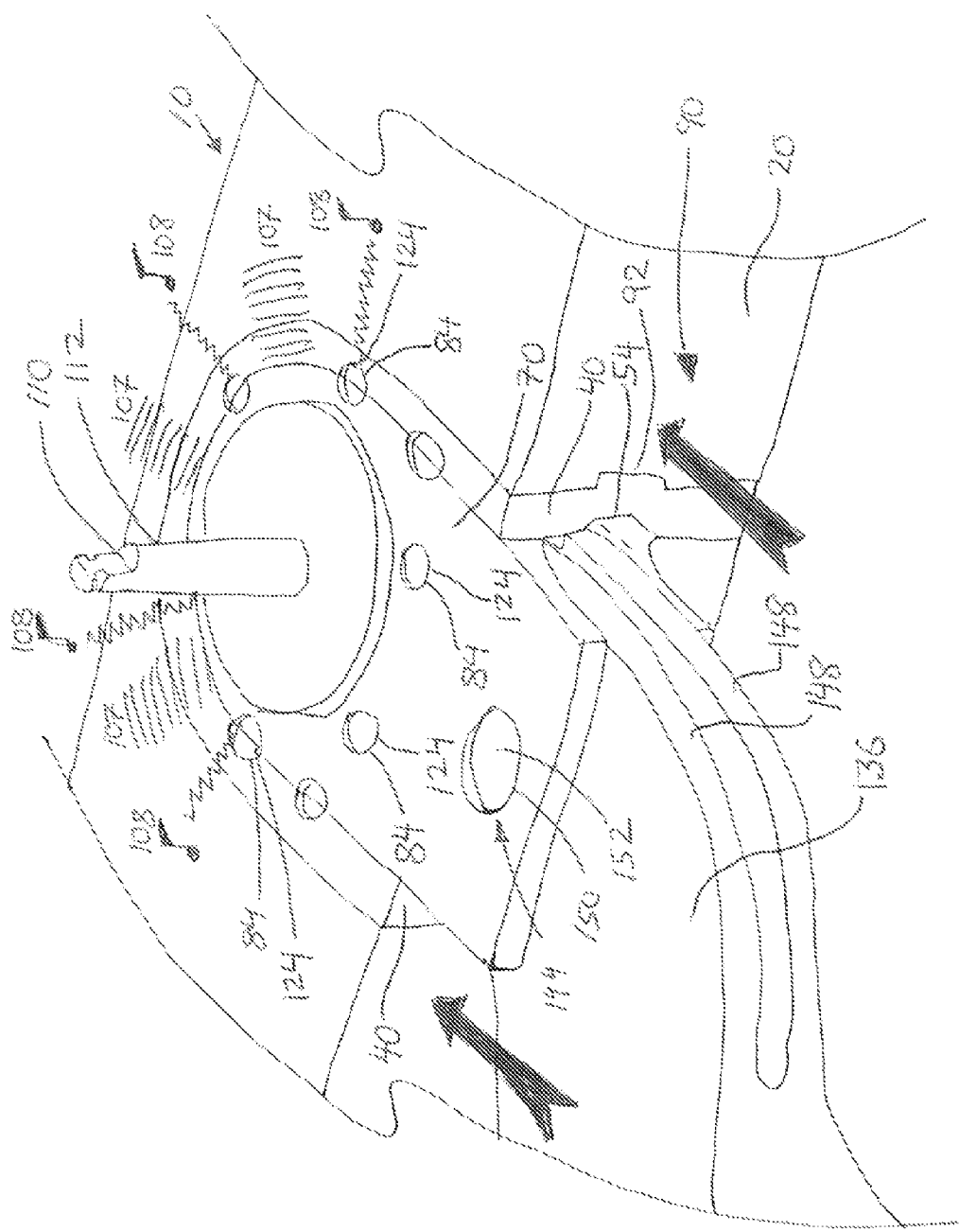

CT-BASED, SIDE-LOADING SURGICAL AND LABORATORY DENTAL IMPLANT GUIDE SYSTEM AND METHOD

CROSS-REFERENCES TO RELATED APPLICATIONS

This application claims the benefit under 35 U.S.C. §119(e) of U.S. Provisional Patent Application No. 61/216,771, filed on May 20, 2009 the contents of which are relied upon and incorporated by reference.

STATEMENT REGARDING FEDERALLY SPONSORED RESEARCH OR DEVELOPMENT

Not Applicable

REFERENCE TO A "MICROFICHE APPENDIX"

Not Applicable.

FIELD OF THE INVENTION

The present invention may relate to dental implant systems that use CT technologies to obtain data from a patient's oral cavity to create a surgical implant guide that is used for the preparation and insertion of an implant into a patient's mouth.

BACKGROUND

Some of dentistry's greatest technological advances occurred in the late fifties and early sixties with the initial development of dental implant and prosthetic technology. This technology provided an alternative to the old method of tooth extraction and replacement dental prosthetics (e.g., removable prosthetics such as dentures held in place by adhesive or suction and non-removable prosthetics such as bridges that are affixed to remaining healthy teeth). The older method generally had reached its limitations at that time in that hand-created and fitted dentures could be easily dislocated and make embarrassing "clicking" sounds; contribute to bone loss; and could be ill fitting and painful. Bridges could be uncomfortable and annoyance to the patients in their means of attachment as well as possibly damage healthy teeth to which they were attached.

Dental implant technology has made it possible to replace the extracted tooth with a prosthetic or artificial tooth (e.g., a crown) that is anchored in the bone of the mouth. In this technology, an anchoring means is generally a dental implant comprising of a specially-shaped and constructed post (generally made of titanium, whose qualities allow it to bond well with the bone-a process called osseointegration) that is placed into the bone structure of the mouth to act as the "root(s)" of the prosthetic tooth. This placement generally allows a portion of the implant to protrude above the gum line where it is generally surrounded by an structure called an abutment or extension that acts as an adaptive interface for the crown (the prosthetic that is constructed to look like that portion of the tooth, which that is visible in the mouth). This abutment ensures the crown is held in the proper orientation and placement once the crown is permanently affixed to the implant.

Currently, the dental implant technology requires a significant amount of preparation, time, as well as a significant amount of talent, skill, knowledge on behalf of the dental healthcare professional (e.g., the dentist) to ensure that the proper implant placement and proper crown attachment occurs. This is necessary to maintain the patient's correct and proper bite (e.g., the alignment between the mandible and upper plate of the patient mouth.) and to proper dental look. If the proper alignment is not maintained with the newly placed implant, then the patent can be placed into constant pain with misaligned bite as well as suffer premature mandible joint wear. Further, this dental capability is necessary during implant surgery (e.g., drilling, boring, threading the pilot hole for the implant) to prevent damage to critical jaw and facial structures such as the inferior alveolar nerve in the mandible (e.g., the lower jaw).

Traditionally, to accomplish these adjectives, a casting or impression of the patient's mouth is taken, along with dental X-rays to aid in the planning and directing of the implant surgery. To further ensure proper placement of the implant, abutment, and crown, additional new technologies have developed using CT-scanning capability to digitally scan a patient's mouth to create datum data. Using this digital data, plus manual data obtained from castings of the patient's mouth, various specialized 3D Cad/Cam computer programming can recreate a virtual, as well as a physical model, of the patient's mouth to prepare the overall implant surgical plan for placement of one or more dental implant(s) in the patient's mouth.

In addition, an overlaying dental surgical guide, also known as a stent, substantially created in the same manner as the model (using CT scanning data or manual creation), can fit over the patient's teeth, bone surface, or mucosa (if all the teeth are missing). This dental surgical guide could have one or more CT-designed hollow channels containing reinforcement tubes or grommets that generally connect the top of the dental surgical guide to the bottom of the dental surgical guide. The passages or hollow interiors in the grommets can generally guide the dentist's placement of the dental implant appliances (e.g., the tools used to prepare and secure the implant in the patient's mouth). Even when using such a top-loading dental surgical guide, the dental health care professional (e.g., dentist) still needs to possess and exercise considerable skill and artistry to correctly locate, orient, and secure the implant into the mouth bone structure as the dentist still has to properly angle the dental implant appliances correctly though the top-loading dental surgical guide. In this manner, the precision of such systems can be seen as being limited.

Another issue generally effecting implant surgery is that dental surgical guide (either CT-based or manually created) generally adds its own thickness and may substantially limit the availability of oral cavity area that is needed to perform those operations for placing the implant. This current limitation may require the patient to open their mouth even further to accommodate the dental implant appliances and the like than if the dental surgical guide was not employed in the first place. While this may not be much of concern regarding implants for lost forward teeth, it can have significant impact for back teeth implant placement, where the patient may be required to open their mouth wider than normal for implant placement resulting in possible over stretching of the temporal mandible joint with resulting significant discomfort, as well as possible physical injury to the patient.

What is needed therefore is a dental surgical guide that can be created using CT-based three-dimensional imaging of the patients mouth (combined with impression-based models) that allows for precisely created and placed aperture(s) and corresponding grommet(s) within the dental surgical guide that allow the dental surgical guide to incorporate a wide variety of datum or implant placement control factors such setting the depth of the implant, its x, y, and z axial orientations, telemetry, and the like in the mouth's bone structure.

Such incorporation, provided in step with a side-loading dental surgical guide with resultant and high precision locating/locking means, could allow the computer-processed datum/implant placement control factors to be utilized in the orientation and operation of dental implant appliances, implant, and implant-related items. This side-loading dental surgical guide system could further incorporate various operator notification means (e.g., audible, tactile, and the like) to inform the operator when correct placement, orientation, and operation of the dental implant appliance/implant has been accomplished.

To further facilitate the ease of the implant placement, the use of side-loading dental surgical guide system could provide for the relieved insertion of implant appliances, implant, and implant-related items through the side rather than the top of the dental surgical guide to allow for greater operating room in the mouth as well as not requiring the patient to significantly open their mouth further to accommodate the insertion of tools/implant into the dental surgical guide.

With these qualities, the side-loading dental surgical guide system could provide a level of control and precision over the planning, guidance, and placement of the implant to a degree previously unheard. This greatly improved capability could significantly increase the ease of the dental implant operation; reduce the time and number of individual operations required for the dental implant operation; reduce the dental implant placement recovery time while overall, increase the dental healthcare professional's implant surgery capability. Such a capability could accomplish this by significantly replacing a large amount of dental art (skill and talent) ordinarily required for the completion of such dental implant surgical operations with computer-controlled, consistent, accurate, scientific precision. The overall result of such a system could provide affordable implant surgery to significantly greater numbers of the public suffering from tooth loss than ever before.

SUMMARY OF ONE EMBODIMENT OF THE INVENTION

Advantages of One or More Embodiments of the Present Invention

The various embodiments of the present invention may, but do not necessarily, achieve one or more of the following advantages:

the ability to side-load dental implant appliances into a dental surgical guide;

provide a dental implant system that reduces the cost, time, and expertise needed to place an implant in a patient's mouth;

the ability of dental implant system to significantly improved the efficiency of implant dentistry to generally make implant dentistry more affordable to greater numbers of the population;

provide a dental surgical guide that can positively lock-in dental implant appliances to a greater degree of precision and control as compared to other dental surgical guides;

the ability to notify the operator when a dental implant appliance is properly secured into place into the dental surgical guide;

provide an indexing means to notify the operator that the dental implant appliance, dental implant and alike has reached it proper operating specifications relative to surgical implant area or to the surgical implant area analogue of a 3D model of the patient's mouth;

the ability of the indexing means to use visual, tactile, auditory notification means to notify the operator when the correct placement position and orientation of the dental implant appliance/implant has been reached;

the ability of the indexing means to use the lack of visual, tactile, auditory stimulus to notify the operator that the correct placement, position, and orientation of the dental implant appliance/implant has not been reached;

the provide a means to amend a surgical plan and update 3D model of the patient's mouth when the dental healthcare professional places an implant outside the original parameters/specifications of the surgical plan;

the ability to lock in an implant analogue to the surgical guide to replicate in a 3D model of the patient's mouth, the positioning of the out-of-surgical plan placement of implant in a the patient's mouth;

provide an side-loading dental surgical guide that can incorporate a wide variety of datum data obtained from CT-Scans, dental impressions, dental castings of the patient's mouth to control placement and operation with greater than before achieved precision of dental implant appliances and the placement of the dental implants as relative to a implant surgical site;

the ability to combine dental implant appliances with an ambidextrous handle outside of the patient's mouth to better manipulate and lock in the appliances into a side-loading dental surgical guide;

provide a dental surgical guide that reduces the amount the patent has to open wide his mouth to accommodate the placement of dental implant appliances into a dental surgical guide; and the ability to accomplish outside of the patient's mouth certain surgical implant procedures normally accomplished within the patient's mouth.

These and other advantages may be realized by reference to the remaining portions of the specification, claims, and abstract.

Brief Description of One Embodiment of the Present Invention

One possible embodiment of the invention could be a side-loading dental surgical guide comprised of a body with a set of walls, a top portion, and a bottom portion and at least one open-sided channel, the open-sided channel that continuously connects an opening of the one of the set of walls to the top portion and the bottom portion; and at least one open-sided master grommet, the open-sided master grommet having a hollow grommet interior that continuously connects a side opening, a top aperture and a bottom aperture; wherein the open-sided master grommet is placed within a respective open-sided channel to allow a dental tooling head to placed into the master grommet through its side opening.

One possible embodiment of the invention could be a dental implant guide system comprised of an open-sided dental implant guide with a set of walls, a top portion, and a bottom portion and at least one open-sided channel, the open-sided channel that continuously connects an side opening of the one of the set of walls to the top portion and the bottom portion; at least one open-sided master grommet, the open-sided master grommet being so received within a respective open-sided channel that the channel's open side matches up with the side opening of the master grommet; and a tooling head that is received within the open-sided master grommet Yet another embodiment of the invention could be a method of operating an side-loading dental surgical guide comprising of the following steps: providing side-loading dental surgical guide having at least one open-sided channel containing an open-sided master grommet, the open side of the master grommet opening upon the open side of the open-sided channel; providing a tool head that can accommodate a dental implant appliance; moving the tooling head through the open side of the open-sided channel; and placing the tooling head into the master grommet.

Yet another embodiment of the invention could be a dental implant system comprised of an dental implant guide with a set of walls, a top portion, and a bottom portion and at least one channel, that can receive a master grommet; a tooling head that is received within the master grommet; a dental appliance that is movably received within at least a portion of the master grommet; Wherein the master grommet, the tooling head, and dental appliance form an indexing means that locks the dental appliance to prevent the further rotational movement of the dental appliance after the dental appliance has obtained the desired depth and angle of final rotation with respect to either the implant surgical site or the implant surgical site analogue.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

FIG. 3B is substantially a perspective view of showing tooling head locking notification means for the present invention.

DESCRIPTION OF CERTAIN EMBODIMENTS OF THE PRESENT INVENTION

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

Figure 1:
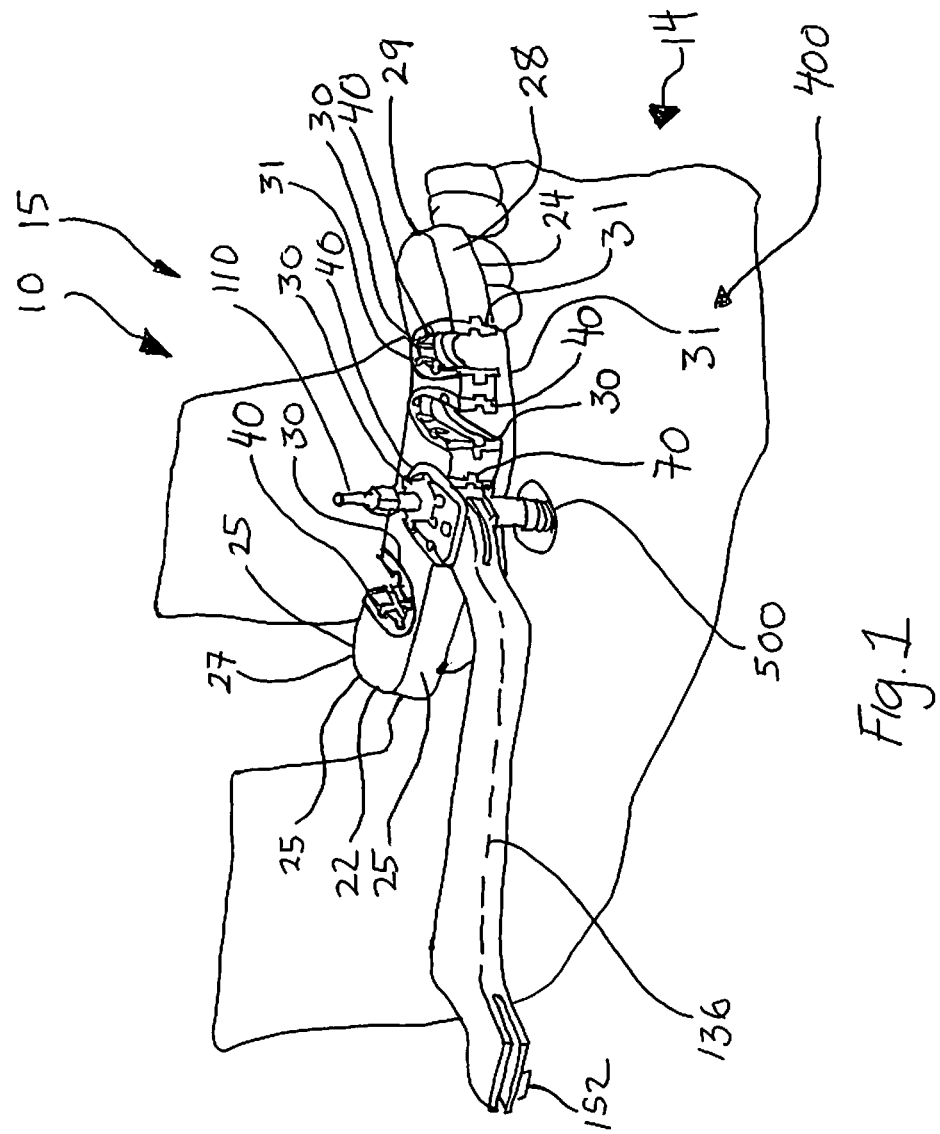
FIG. 1 is substantially a perspective view of one embodiment of the side-loading dental surgical guide of the present invention as it is applied to an operating area of a patient.
Figure 1A:
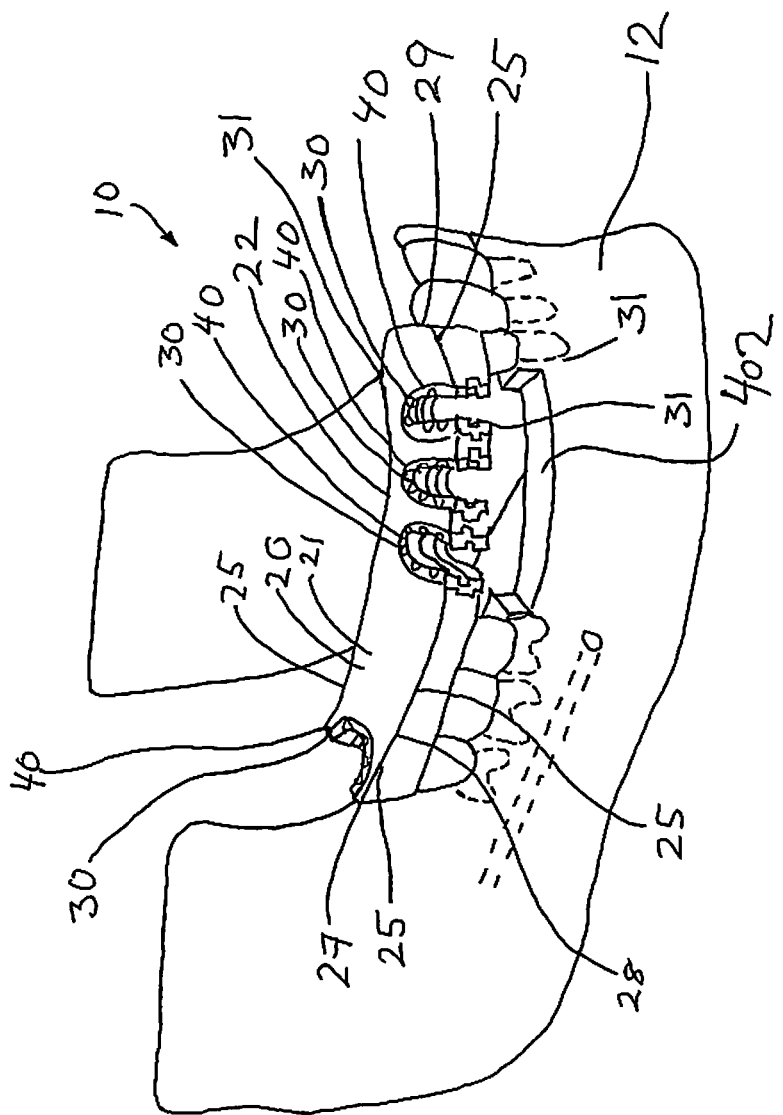
FIG. 1A is substantially a perspective view of one embodiment of the side-loading dental surgical guide of the present invention as it is applied to 3D translucent model.
Figure 2:
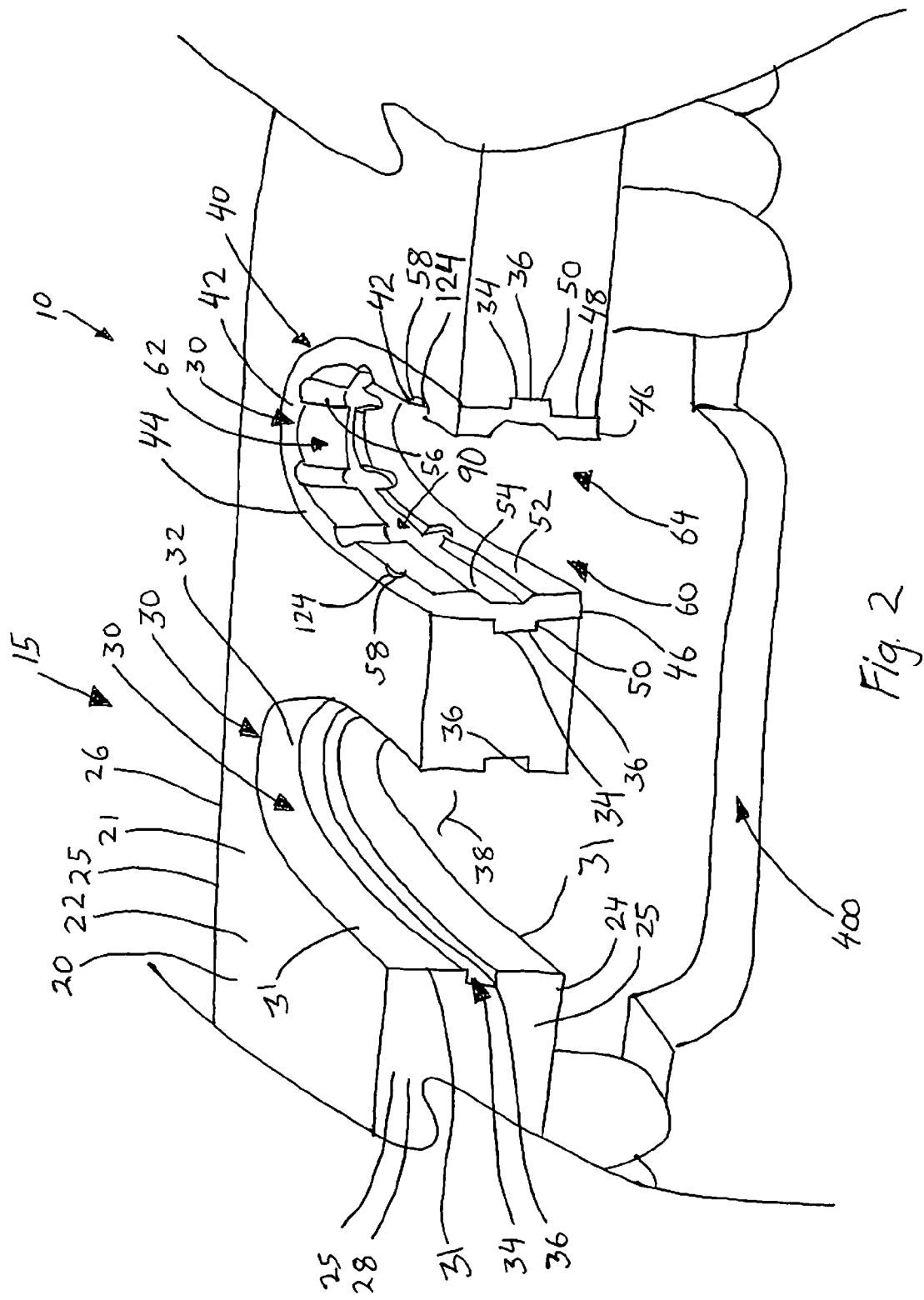
FIG. 2 is substantially a perspective view of one embodiment of the side-loading surgical guide of the present invention.

The present invention 10 generally comprises a CT data-based, side-loading surgical dental guide system 15 with a method for operating same 300. As substantially shown in FIGS. 1, 1A, and 2, the system 15 could at least comprise of a side-loading dental surgical guide 20 generally having channel 30 containing a master grommet 40, wherein at least embodiment the channel 30 could be an open-sided channel 30 and the master grommet 40 could be an open-sided master grommet 40. The system 15 could further comprise of one or more tooling heads 70 that could be reversibly attached and locked into the master grommet 40. The tooling heads 70 being further constructed to hold dental implant appliances 110 to properly prepare, locate, and secure the implant 500 within the bone structure of the patient's mouth/an implant analogue 502 within a model of the patient's mouth 12; and further carry out operations of the surgical implant plan.

In at least one embodiment, the system 15 could further comprise of tooling head-handle 136 that can be reversibly attached to one or more tooling heads 70 for aid in manipulating the tooling head(s) 70 (e.g., along with attached dental implant appliances 110) relative to its placement within with the side-loading dental surgical guide 20.

The side-loading dental surgical guide 20 could be created using at least datum data obtained from CT scan [e.g., CBCT or Cone Beam Volumetric Image or other suitable DICOM (Digital Imaging and Communications in Medicine) scanning means] of the patient's mouth. In at least one embodiment, the digital scan data could further augmented with data acquired from manual/physical recordation of the patent's mouth (e.g., a dental impression and resulting casting). All of this data could be processed and integrated by one or more virtual implant planning software programs to create a virtual model of the patient's mouth, the virtual model being used to plan the dental implant surgical plan. These programs can be further used in conjunction with various manufacturing software programs and systems to render a physical model 12 (e.g., transparent/translucent model) of the patient's mouth, which can also be also used in dental surgical planning as well as for verifying physical various aspects of the implant dental surgical plan. Generally in the same manner, the side-loading dental surgical guide 20 (e.g., stent) of the invention 10 can be produced using computer-controlled standard acrylic methodologies or rapid prototype manufacturing means. In this manner, the side-loading dental surgical guide 20 can be placed on the translucent physical model 12 (having a modeled or surgical implant site analogue 402) to indirectly verify fit of the side-loading dental surgical guide 20 to the implant surgical site 400 of the patent's mouth 14 as well as make adjustments both to the implant dental surgical plan and the related-dental implant appliances 110 (e.g., implant analogue 502) of the invention 10 as used in conjunction with the side-loading dental surgical guide 20 of the invention 10.

The side-loading dental surgical guide 20 could comprise of a body 21 having a top portion 22, a bottom portion 24, and a set of walls 25. The set of walls 25 could include an inside guide wall 26 (e.g. the lingual wall, which generally faces the tongue or palate area of the mouth); a first end wall 27, an outside guide wall 28 (the buccal wall, generally facing the cheek/lips area) and a second end wall 29. The bottom portion 24 could be substantially configured to rest upon one or more of the patient's teeth; bone; and/or mucosa (e.g., if no teeth are left in that portion of the mouth 14 to which the guide 20 is to be applied) or a replica of same in the model 12 of patient's mouth, so as to substantially located the guide 20 adjacent to the implant surgical site 400/implant surgical site analogue 402. The body 21 of the dental surgical guide 20 could further one or more open-sided channels 30 created for receiving a respective master grommet 40 that could be used receiving the tooling head 70 that could contain an implant appliance 110 (e.g. for placement of dental implant 500/dental implant analogue 502, and the like.) One or more open-sided channels 30/master grommets 40 could be located proximate to one or more of the walls 25 to substantially allow a tooling head 70 to be generally received by the dental surgical guide 20 through one or more side openings 60 located proximate to a wall 25.

In at least one embodiment, the open-sided channel 30 could further defined by a channel wall 32 of the dental surgical guide 20, the channel wall 32 generally having a U-shaped or horseshoe-shaped lateral cross-section. The open-sided channel 30 could continuously connect openings 31 in the top portion 22, a wall 25 (e.g., the outside guide wall 28, the inside guide wall 26, end walls 27, 29) and the bottom portion 24 to a generally hollow channel interior 38.

In at least one embodiment, at least one open-sided channel could receive a reciprocal, specifically-designed the open-sided master grommet 40. The master grommet 40 could have a grommet body 42 that is made from titanium or other suitable material known in the art could generally have a U-shaped or horseshoe-shaped configuration to be substantially reciprocal to the U-shape of its respective channel 30 to substantially allow the grommet body 42 to be generally nestled within the open-sided channel 30. The grommet body 42 could further comprise of a grommet top 44, a grommet bottom 46, an exterior grommet wall 48, and an interior grommet wall 52.

The interior grommet wall 48 could further define a grommet interior 66 that is generally hollow, wherein the grommet interior 52 substantially and continuously connects a side opening 60 on a side of the grommet body 42 with a top aperture 62 formed by the grommet top 44 and with a bottom aperture 64 formed by the grommet bottom 46.

In at least one embodiment, the dental surgical guide 20 could employ one or more master grommet locating means 34. The master grommet locating means 34 could be used to exactly locate and lock into place a specifically-designed and created open-sided master grommet 40 within its reciprocal, specifically-designed and created, open-sided channel 30 (e.g., through the establishment of tight tolerance fit between the opened channel 30 and its respective master grommet 40 in conjunction with master grommet locating means 34). In this manner, the compiled computer datum data of the patient's mouth 12 as applied to creation of the side-loading dental surgical guide 20 can be further imparted into the design/creation of the corresponding master grommet 40 (and hence respective tooling heads 70) to guide with generally previously unavailable precision and accuracy the placement and orientation (e.g., telemetry, height, position, angle of rotation, and x, y, z axis data) of the dental implant appliances 110 (hence implant 500/implant analogue 502) relative to the desired implant surgical site 400/modeled implant surgical site analogue 402.

One version of the master grommet locating means 34 could comprise of a laterally (e.g., horizontally) located, locking groove 36 that is radially cut into the channel wall 32 to substantially receive and lock into a reciprocal, laterally located, radially disposed tongue 50 or protrusion located on an exterior grommet wall 46 of the master grommet 40. Additionally, dental adhesives (e.g., acrylic type) known to those who have ordinary knowledge in the art can be further applied to generally secure the open-sided master grommet 40 into its respective open-sided channel 30.

Although the figures generally show the channel 30 and its respective master grommet 40 with their respective longitudinal axis in a generally vertical orientation with respect to the dental surgical guide 20, it should be noted that the channel 30 can be created within the dental surgical guide 20 and oriented to allow a wide range of positioning (including various non-vertical placements) for the tooling head 70 and respective implant appliances 110 (e.g., to substantially allow a non-vertical angled placement of an dental implant 500 in the patient's mouth 12 for better anchoring if a vertical placement of dental implant 500 would place the dental implant 500 in insufficient bone mass to hold the dental implant 500 properly in place in the mouth 14.)

Figure 3:
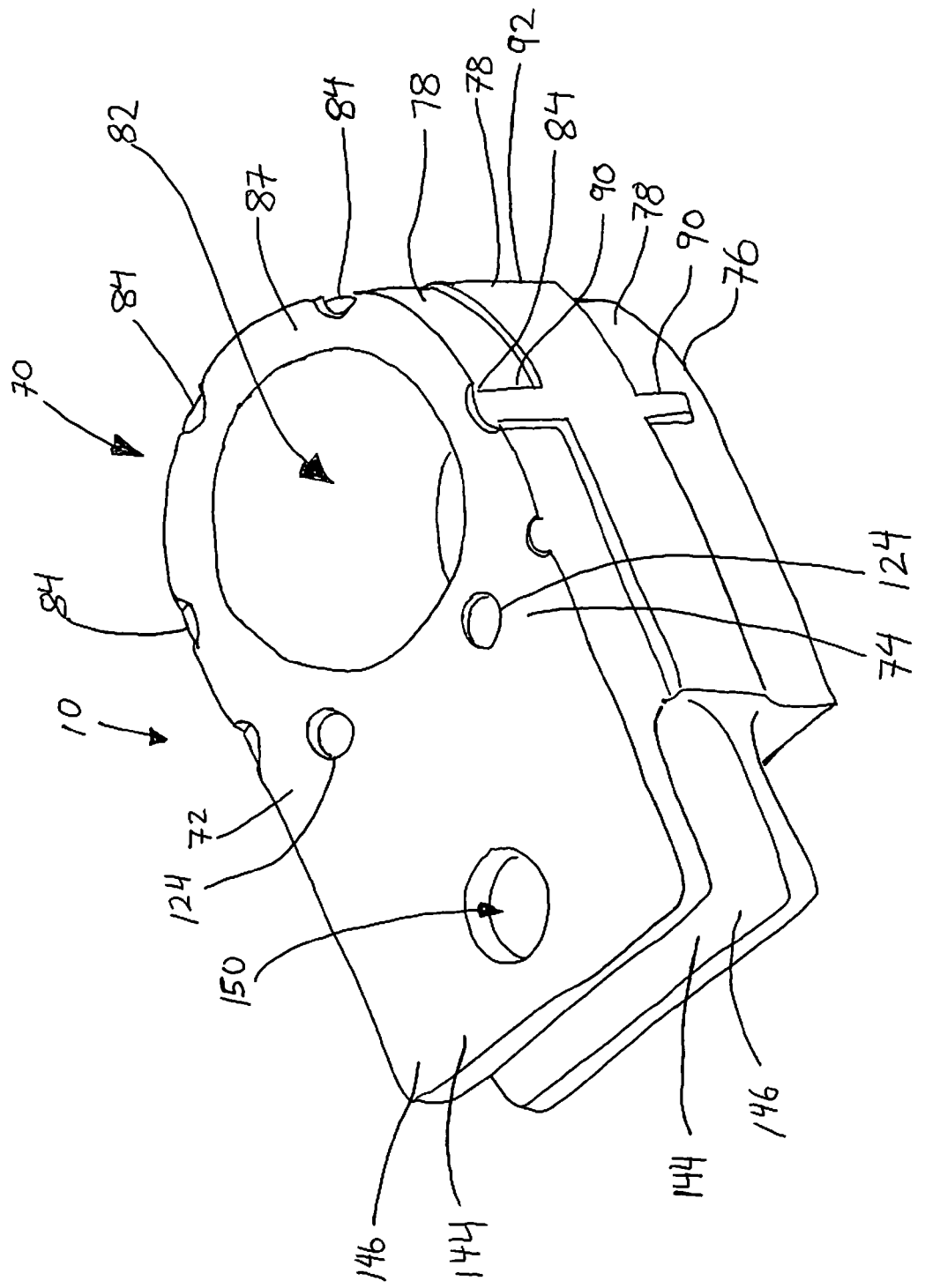
FIG. 3 is substantially a perspective view of the tooling head of the present invention.
Figure 3A:
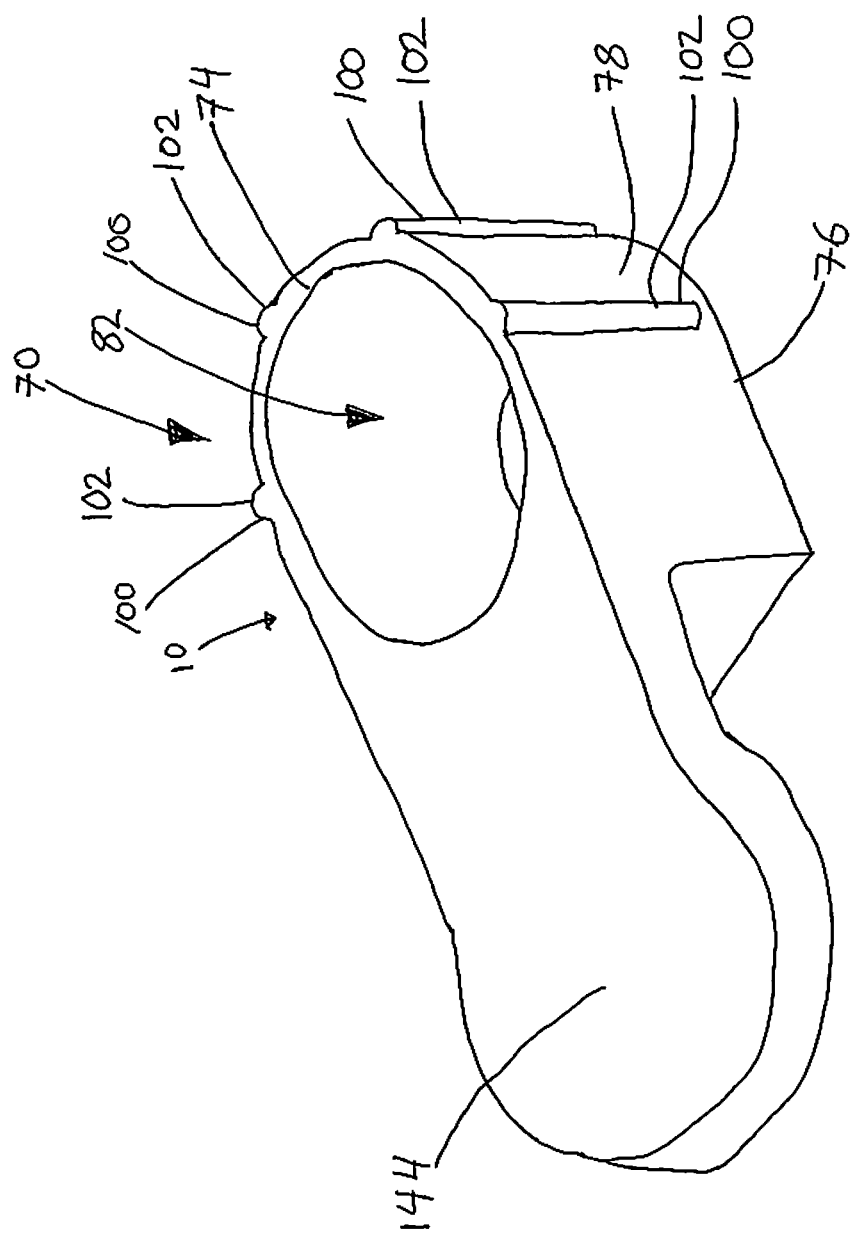
FIG. 3A is substantially a perspective view of another embodiment of the tooling head for the present invention.

As generally shown in FIGS. 3 and 3A, the tooling head 70 could comprise of a tooling head body 72 having a head top 74, a head bottom 76, an exterior head wall 78, and an interior head wall 80. The interior head wall 80 could further define a double-open ended, vertically oriented, head channel 82 continuously connecting the head top 74 with the head bottom 76. The head channel 82 could be designed and constructed to accommodate a wide variety of dental implant appliances 110 and the like (e.g., providing the form for making an implant abutment; providing a guide for placement of implant analogues 502; etc.) as needed. The tooling head body 72 could generally have a U-shaped lateral cross section so that when it is placed within the hollow interior 38 of the open-sided master grommet 40, the rounded portion of the exterior head wall 78 could match up to and nestle next to the interior grommet wall 52.

As generally shown in FIG. 3B, the invention 10 could further feature a tooling head locking means 90 for reversibly securing with previously unobtainable precision and accuracy a tooling head 70 (e.g., that could containing dental implant implement 110) to the interior grommet wall 52 of a respective open-sided master grommet 40. The invention 10 could also further comprise of a tooling head depth locking means 100 for locating the height and orientation of the tooling head 70 (e.g., containing the dental implant appliances 110) within the open-sided master grommet 40 itself.

In at least one embodiment, the tooling head locking means 90 in one embodiment could be at least a radially-disposed grommet groove 54 laterally located on the interior grommet wall 52 that substantially receives a corresponding radially disposed belt 92 laterally located on an exterior head wall 78 of a tooling head 70 (e.g., both parts can be engineered with close tolerances to carefully control with great precision the positioning and orientation of a specific tooling head 70 within a respective open-sided master grommet 40).

In at least one embodiment, the tooling head depth locking means 100 could comprise of a series of vertical ridges 102 radially disposed in parallel orientation around the exterior head wall 78 of the tooling head 70 that can be placed into a corresponding set of matching vertical grooves 56 located on the interior grommet wall 52. The vertical grooves 102 could be constructed so that the top of the vertical grooves 56 do open up at the grommet top 44, while the bottom of the vertical grooves 56 do not open up at the bottom of the tooling head 70. In this manner of creating a specific distance between the bottoms of these vertical grooves 56 and the grommet bottom 46, could create a register that can be precisely engineered to control how far down an inserted tooling head 70 sits in its respective master grommet 40 (e.g., as well as control the overall rotation and other orientation factors of the tooling head 70 relative to the dental surgical guide 20.) The tooling head depth locking means 100 could be applied to those tooling heads 70 that lack the belt 92 and are generally inserted through top aperture 62 rather than the side opening 60 to be loaded into a respective master grommet 40.

As substantially shown in FIG. 3B, at least one embodiment of the invention 10 could further comprise a tooling head locking notification means 106 whereby when the tooling head 70 is inserted into place in its respective open-sided master grommet 40, the tooling head locking means 90 (e.g., the grommet groove 54 and the tooling head belt 90 could be engineered in their tolerances to provide that generally during the physical action of their mating, (e.g., a "force fit" insertion of the belt 90 into place into the groove 54) could further impart to the operator a notification. Such a notification (e.g., auditory, tactile, etc) could indicate that the mating took place successfully. Conversely, a lack of such a notification during such operations could indicate to the operator that the mating of tooling head 70 with the open-sided master grommet 40 did not take part successfully. An auditory notification could be a "clicking" sound 108, while the being tactile notification could be a vibration 107 transmitted though the tooling head 70 to be generally felt by the operator who is generally holding the tooling head 70/attached tooling head-handle 136.

Figure 4:
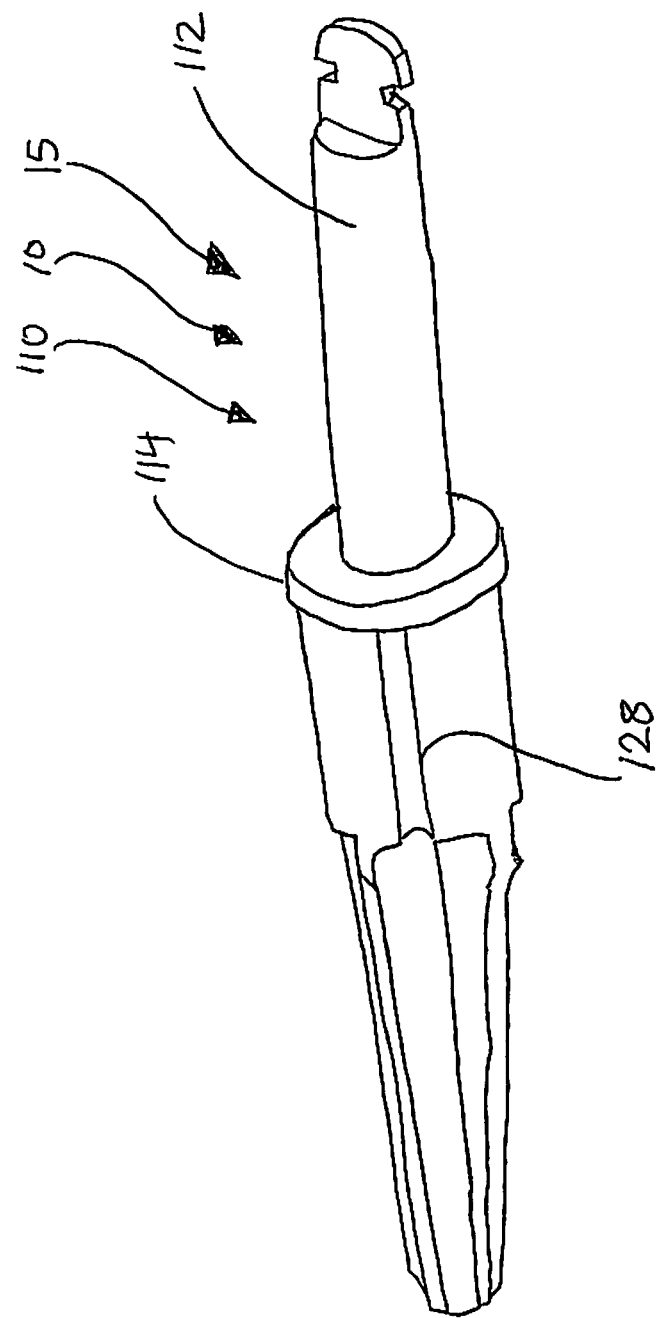
FIG. 4 is substantially a perspective view for a dental appliance of the present invention.
Figure 4A:
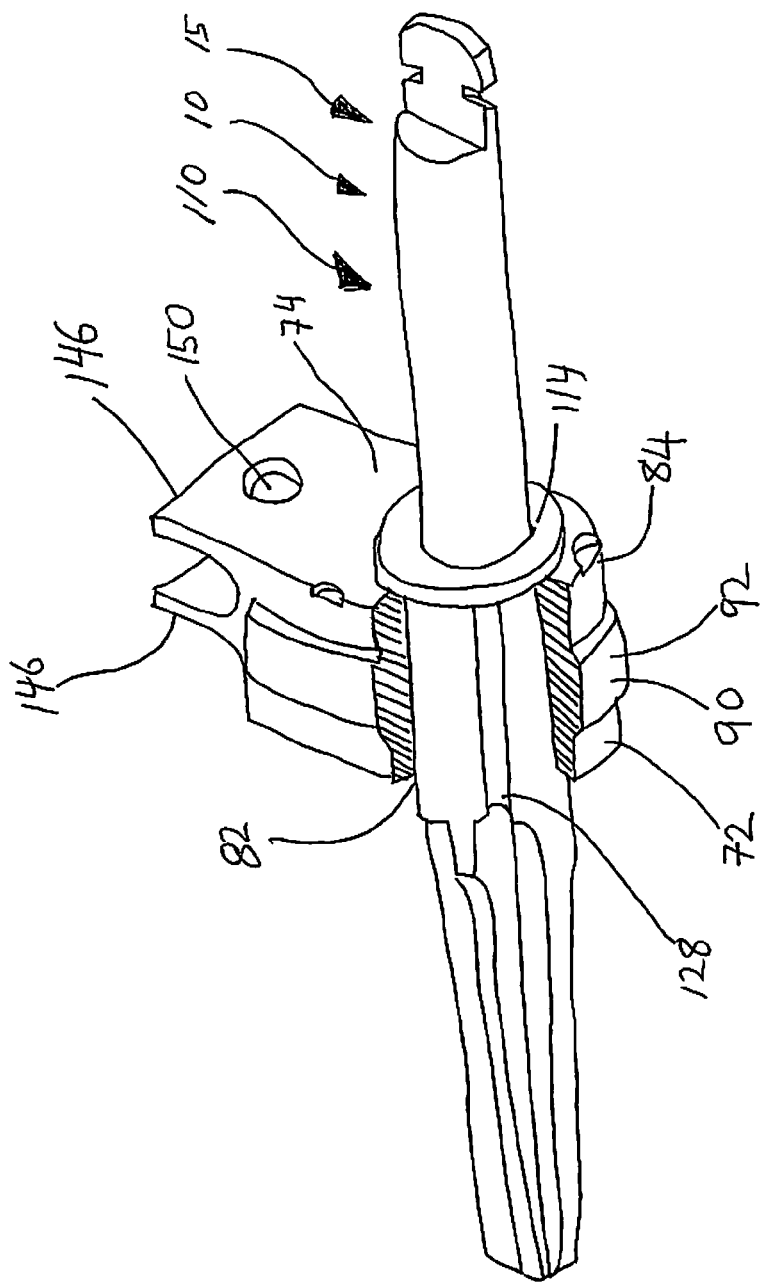
FIG. 4A is substantially a perspective cutaway view for a dental appliance in combination with a tooling head.
Figure 5:
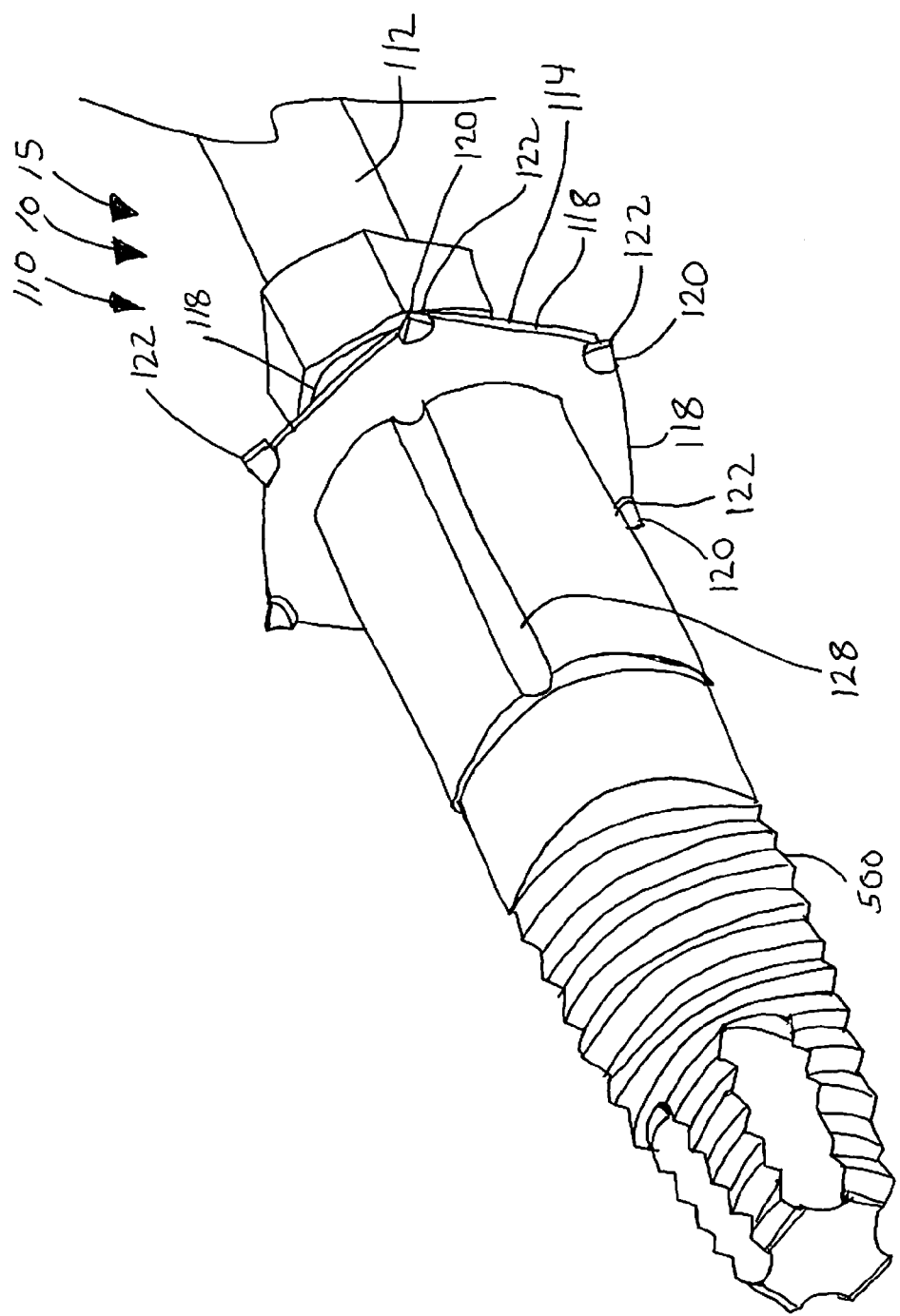
FIG. 5 is substantially showing a perspective view of another embodiment of the dental appliance of the present invention.

As substantially shown in FIGS. 4, 4A, and 5, the tooling head 70 could be designed to accommodate a wide variety of well-known dental implant appliances 110. One set of dental appliances 110 could be those used to prepare the implant surgical site 400 for receiving the implant 500 (e.g., (e.g., tissue punch, cortical perforation counter sink, starter drills, final step drill, etc); another possible set could be dental implant appliances 110 for the placement of the implant 500; another set could be used for creating the abutment for the implant 500; another set could be dental implant appliances 110 used to set implant analogues 502 in the translucent 3D model 12; and the like.

In many instances, these implant appliances 110 have body 112 with an overall shaft-like construction with an operation end and a powered end. Further, these dental implant appliances 110 generally can further comprise of a collar 114 upon the body 112, the collar 114 having a radial orientation substantially perpendicular to the dental implant appliance's longitudinal axis. The dental implant appliances 110 could place their operation end into and through the tooling head channel 82 (generally such placement could be done outside of the patient's mouth) wherein the collar 114 generally acts as a precise locking/notification tool that substantially limits the dental appliance's total passage through and around rotation within the channel 82 so to generally control the operational depth, degree of rotation, and the like of the dental implant appliance 110 relative to the implant surgical site 400 of the patient's mouth 14 or the implant surgical site analogue 402 of the translucent 3D model 12.

The operation end of the implant appliance 110 operates on the implant surgical site 400 (or the implant surgical site analogue of the translucent 3D model 12) or connects to the implant 500 (e.g., drill head, tissue cutting head, etc.). The other end of the dental implant appliance 110 could be constructed for reversible attachment to the dental air power tool or dental manual operated ratchet to rotate the dental implant appliance 110 around its longitudinal axis within the tooling head 70 or otherwise move the dental implant appliance 110 in relationship to the tooling head 70 (e.g., control in-and-out movements of the dental implant appliance 110).

Additionally, some of these dental implant appliances 110, due the tight tolerance fit of the implant appliance 110 to the respective tooling head channel 82, may further comprise of a longitudinally-oriented blood groove 128 that is substantially located on the body 112. The blood groove 128 that would direct out of the tooling head channel 82 any blood, viscera, and the like (e.g., coming from the implant surgical site 400) that otherwise could enter into the channel 82 and otherwise bind up or seize the dental implant appliance 110 within the channel 82. As substantially shown in FIG. 5A, to further control the depth in which the dental appliance 110 operates, the invention 10 may further comprise a dental implant appliance indexing means 116. For those implant appliances 110 requiring very precise depth control and rotational degree control such as the thread cutter, implant placement tool, and a like, this dental implant appliance indexing means 116 could be instituted by having the collar 114 to be constructed in such a manner as to have multiple (e.g., six) edges 118, with each respective pair of edges 118 forming a corner 120 with a tab 122 at each of the corner 120. The means 116 could further comprise of a set of grommet top depressions 58 and a set of tooling head depressions 84 which may align together to substantially form a set or ring of dimples 124 radially arranged around the top aperture 62 of the tooling head channel 82. As the implant appliance 110 is generally rotated with the tooling head channel 82 (e.g., into the implant surgical site 400) each dimple 124 could receive one a respective tab 122. As each tab 122 locks into its respective dimple 124, this could stop the rotation of dental implant appliance 110 within the tooling head channel 82 to place the dental implant appliance 110 with great precision at desired depth relative to the implant surgical site 400 and at a specific degree or final angle of rotation.

Figure 5A:
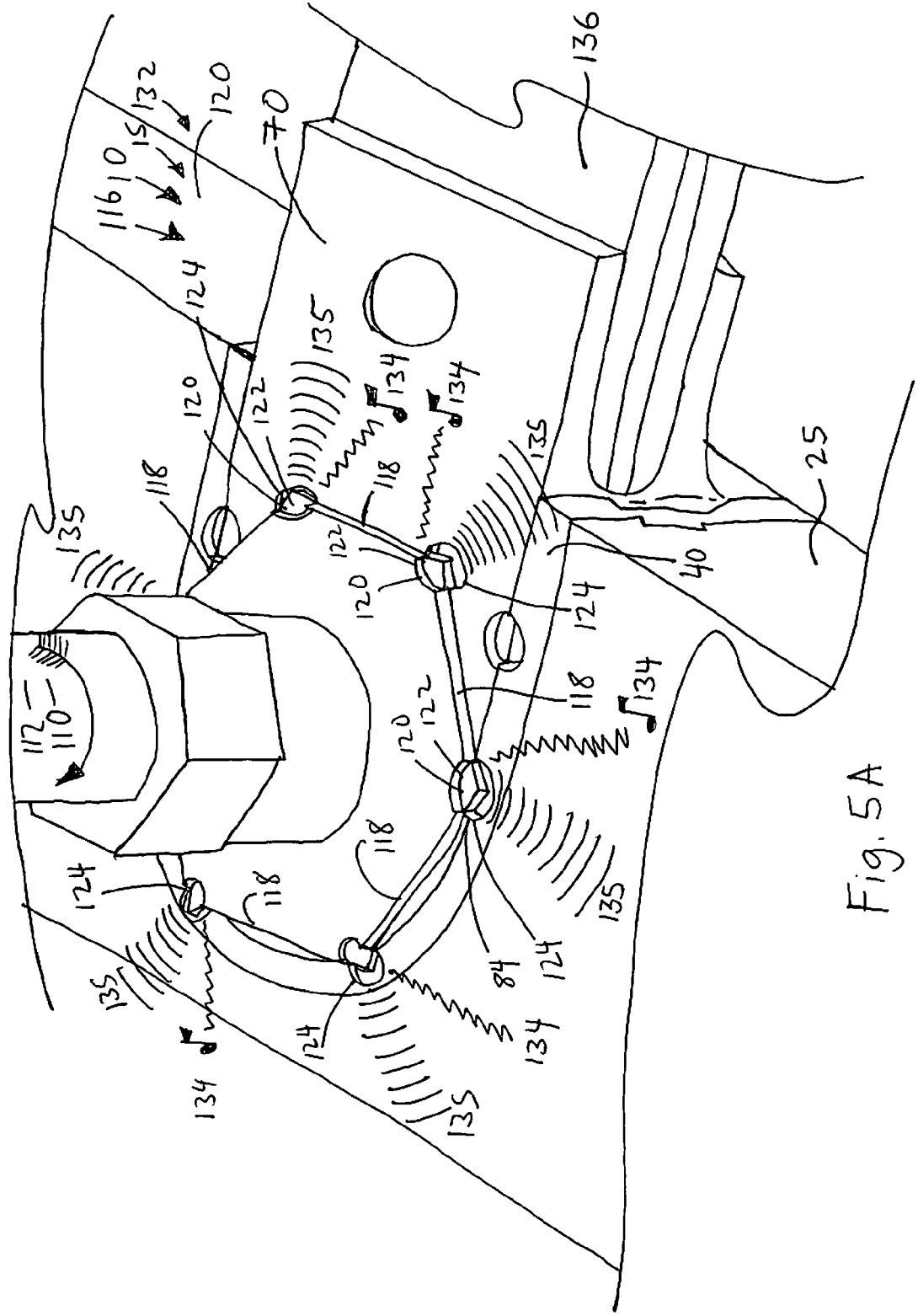
FIG. 5A is substantially showing a perspective view of dental appliance indexing means of the present invention.

As substantially shown in FIG. 5A, the surgical guide system 15 could further comprise of an dental appliance notification means 132 wherein the dental implant appliance indexing means 116 could further incorporate through its tolerances that when the desired operational position of the dental implant appliance 110 relative to the tooling head 70 and its corresponding open-sided master grommet 40 had been properly obtained (e.g., the tabs 122 moving into and fitting into the respective dimples 84 with sufficient force) this action, besides interlocking the dental appliance 110 relative to the dental surgical guide 20, could result in the creation and issuance of an audible notification (e.g., a "click" sound 134) to the operator indicating that desired operating position/orientation of the dental implant appliance 110 (e.g., as well as desired operating position of the implant 500 had been properly achieved). Similarly, the vibration 135 created from the fitting of the tabs 122 as they slide from the tooling head top 74 into their respective dimples 84 could in itself be created and issued/transmitted through the tooling head 70 (and any attached handle 136) directly to the operator as its own tactile notification of proper operational positioning of dental implant appliance 110 and the like. The placement of the tabs 122 within their respective dimples 84 could further provide a visual indexed confirmation for the operator that the dental implant appliances 110 had obtained the previously determined-desired operating position and orientation.

The failure of such notification to occur during operations could also act as a converse notification to the operator of the failure of the dental implant appliance 110 to obtain the proper operational positioning/orientation during the execution of the dental implant surgical plan. Once notified the operator could implement the necessary steps to rectify said failure.

Figure 6:
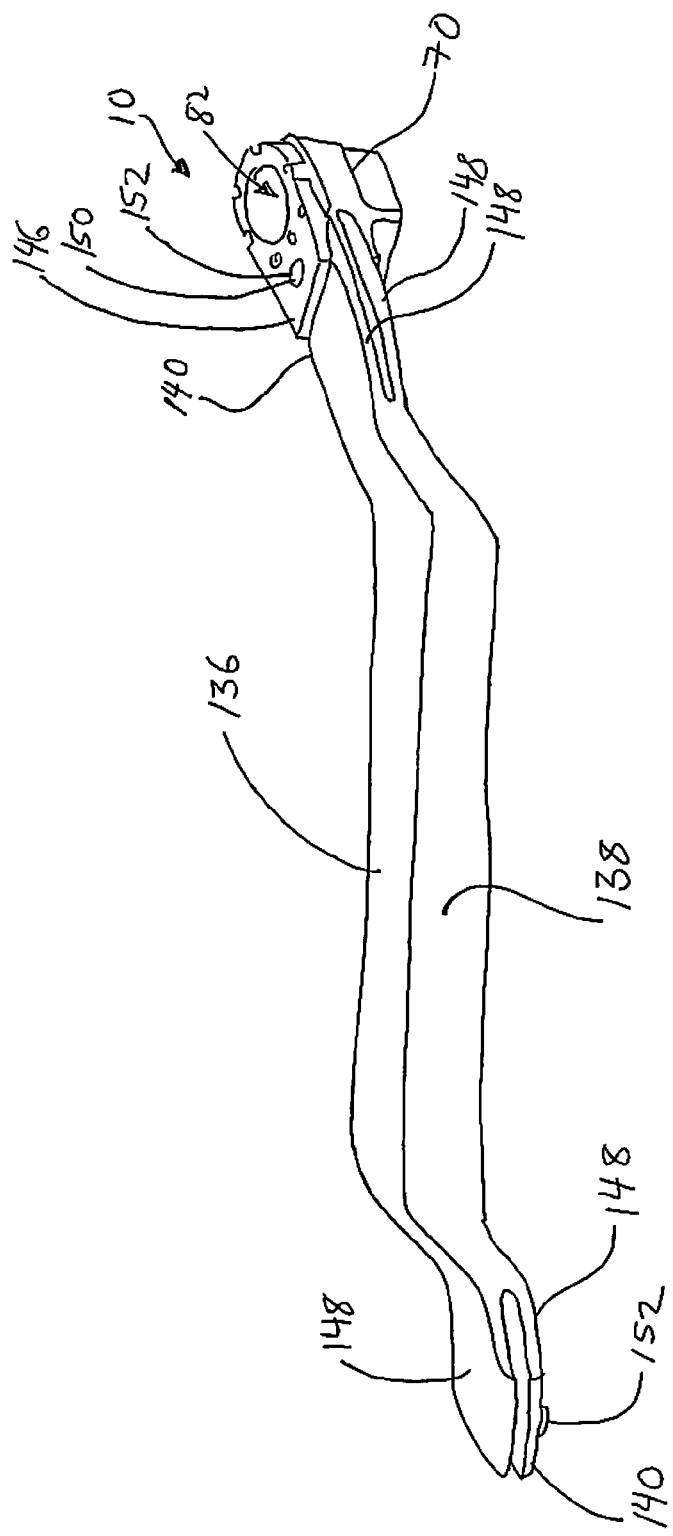
FIG. 6 is substantially a perspective view of handle of the present invention.

As shown in FIG. 6, the surgical guide system 15 could further comprise of a tooling head-handle 136 used in the manipulation of the tooling head 70 relative to its corresponding master grommet 40. The handle 136 could have a body 138 of an ambidextrous design with an overall S-shape and could be made from titanium. In addition to manipulating the tooling head 70/dental implant appliance 110, the tooling head-handle 136 with its curved ends 140 could be used to suitably position the corners of the patient's mouth and the like relative to the dental implant surgery.

In at least one embodiment, for the reversible attachment of the tooling head 70 to the handle 136, the system 15 could further comprise of one or more tooling head-handle attachment means 144 to reversibly secure the tooling head 70 to a suitable tooling head-handle 136. In at least one embodiment, these attachment means 144 could be a set of parallel spaced tabs 146 attached to and protruding outward from a exterior tooling head wall 78 and a corresponding set of prongs 148 that may be spaced parallel and apart from one another, the prongs 148 generally further attached to and protruding outward form a respective curved end 140 of the handle 130. One tab 146 could be proximate to the top of the tooling head 70 and generally in the same plane as the top 74 of the tooling head 70 while the other tab 146 may be located proximate to the middle of the tooling head body 70.

In the center of each tab 146 could be a tab aperture 150 that could receive a respective raised prong dimple 152 of its corresponding prong 148. The set of prongs 148 could be reversibly inserted between the corresponding set of tabs 146 as tooling head 70 is reversibly connected to the tooling head handle 136. The tab aperture 150-prong dimple 152 combination could provide the necessary friction fit to reversibly, yet securely, hold the tooling head 70 onto a curved end 140 of the handle 136.

Figure 7:
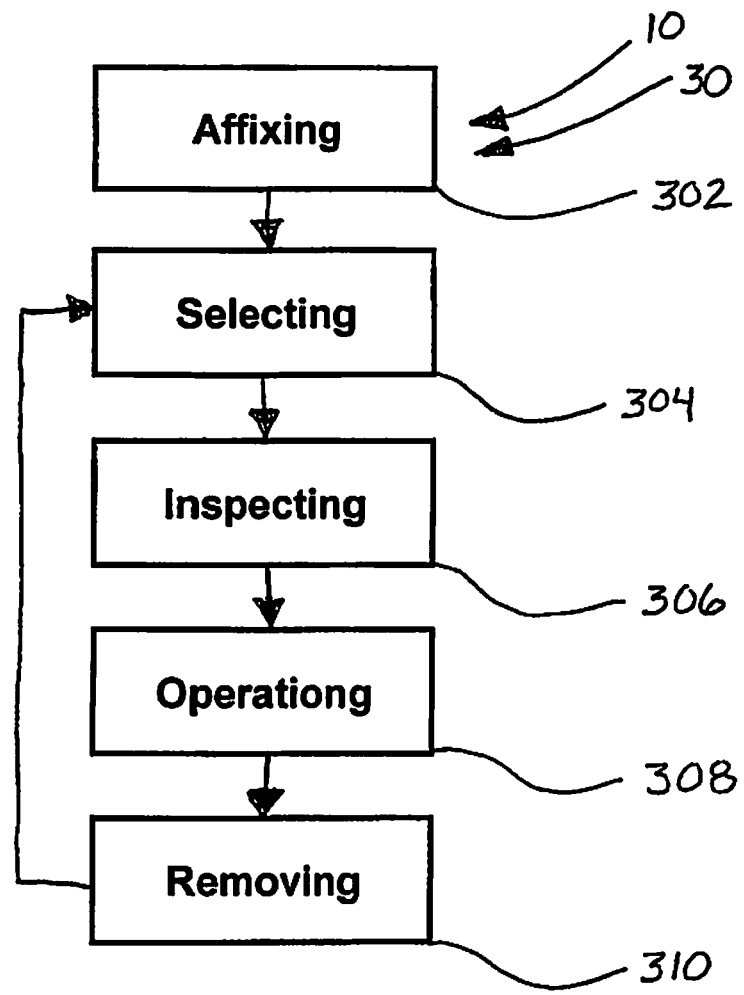
FIG. 7 is substantially showing a flow chart for one embodiment of the method for operating the invention.
Figure 8A:
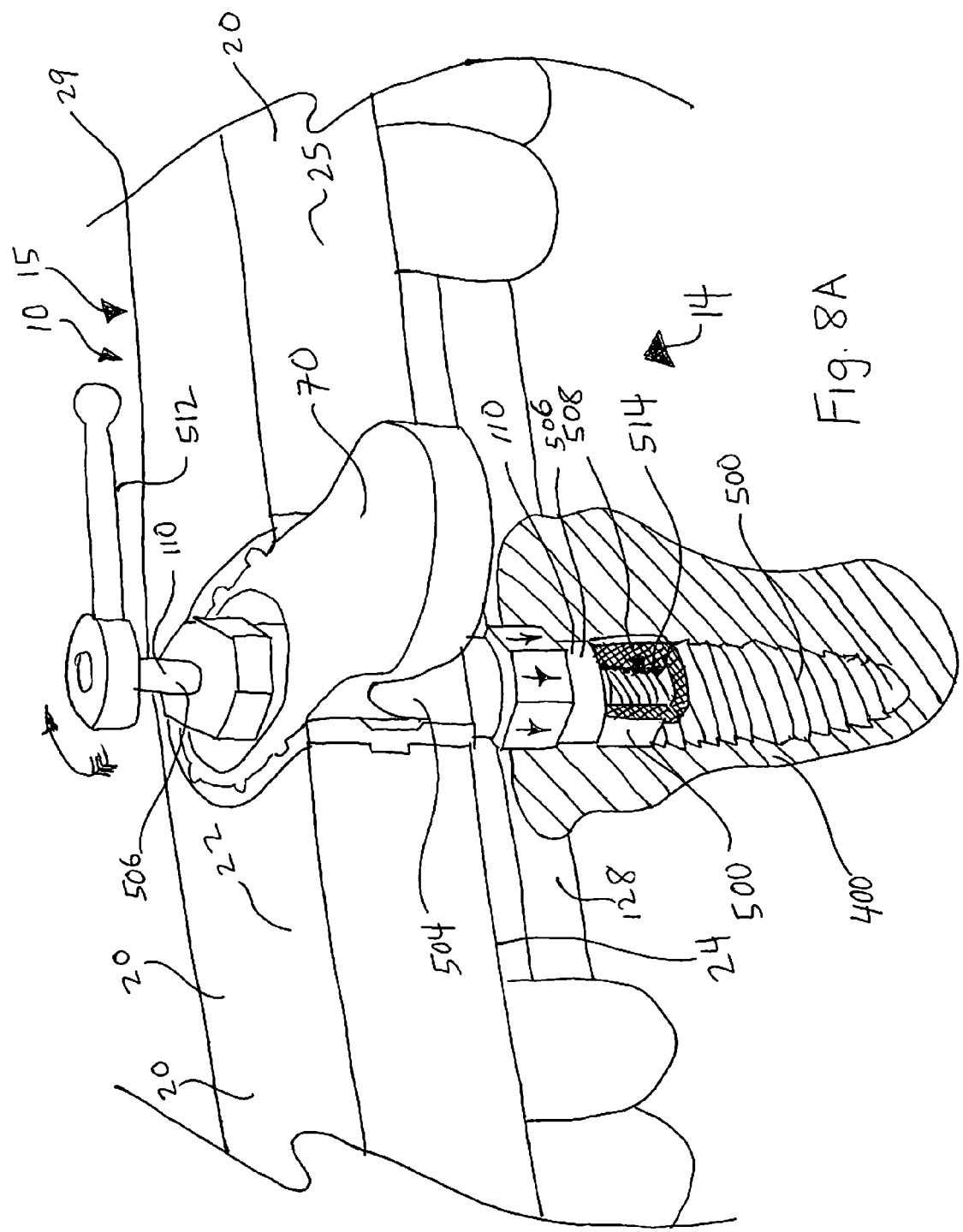
FIGS. 8A-8F are perspective cutaway views substantially showing the process using placement of an implant analogue in the translucent 3D model to representing the real life placement of the implant outside of the parameters of the surgical plan.
Figure 8B:
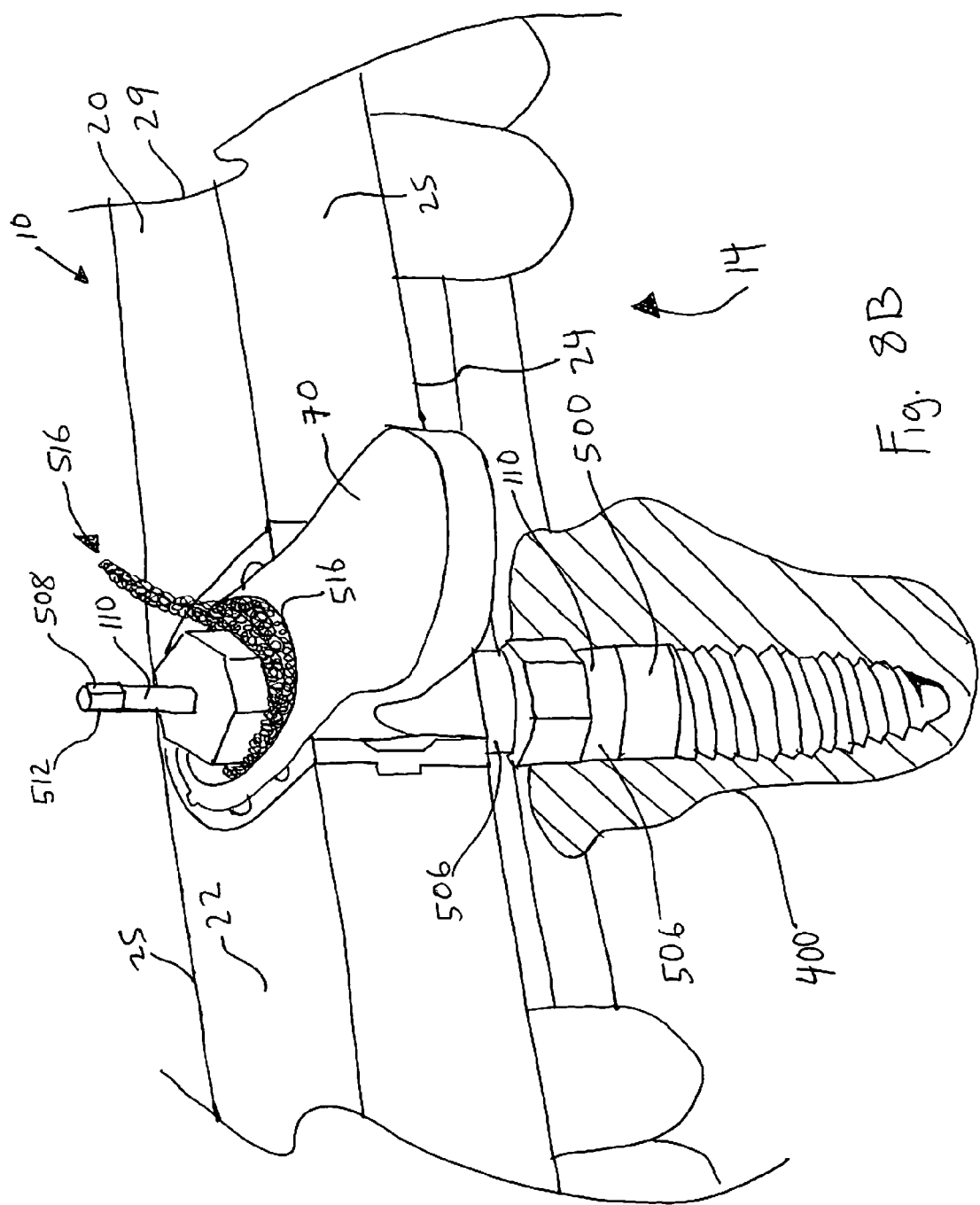
Figure 8C:
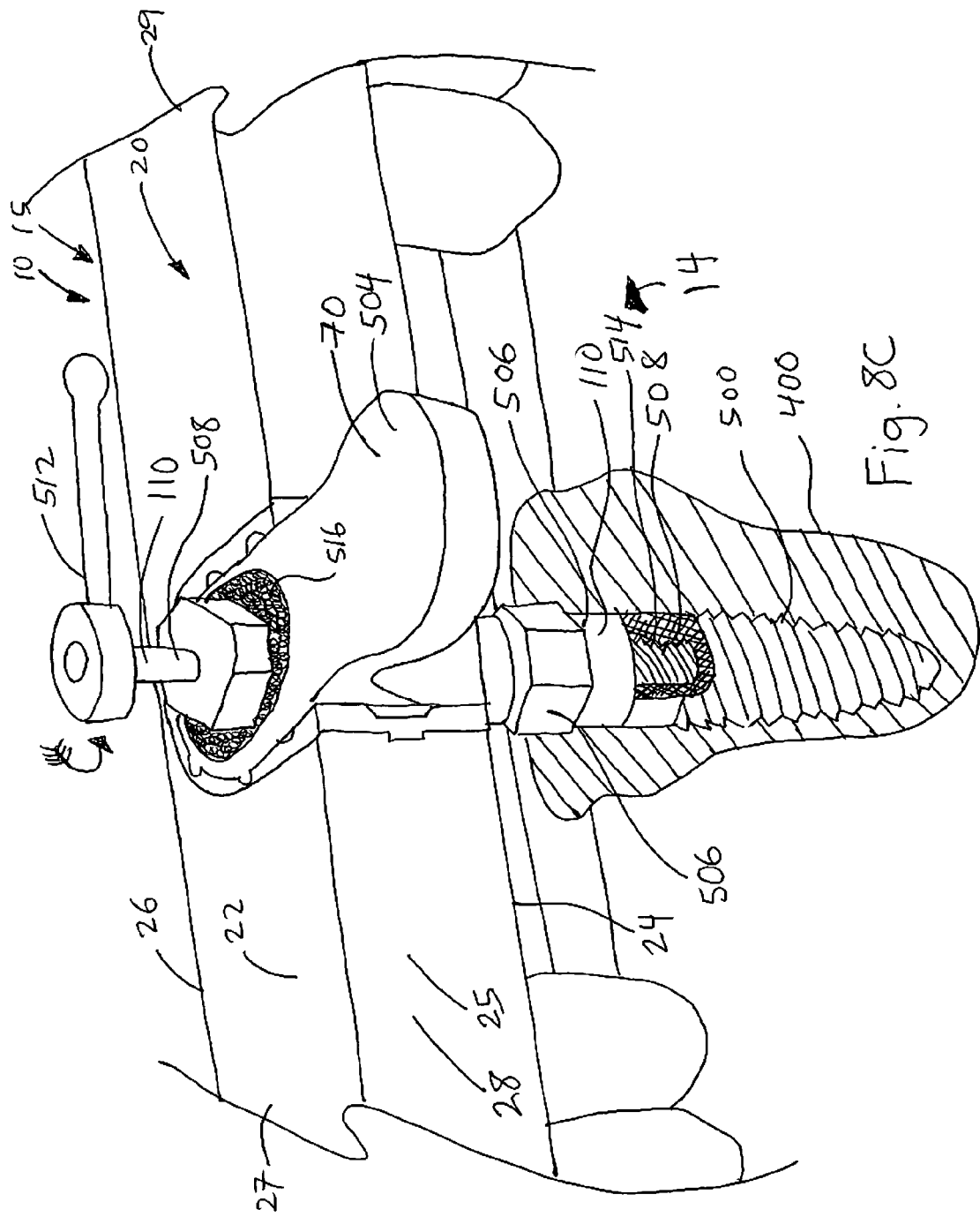
Figure 8D:
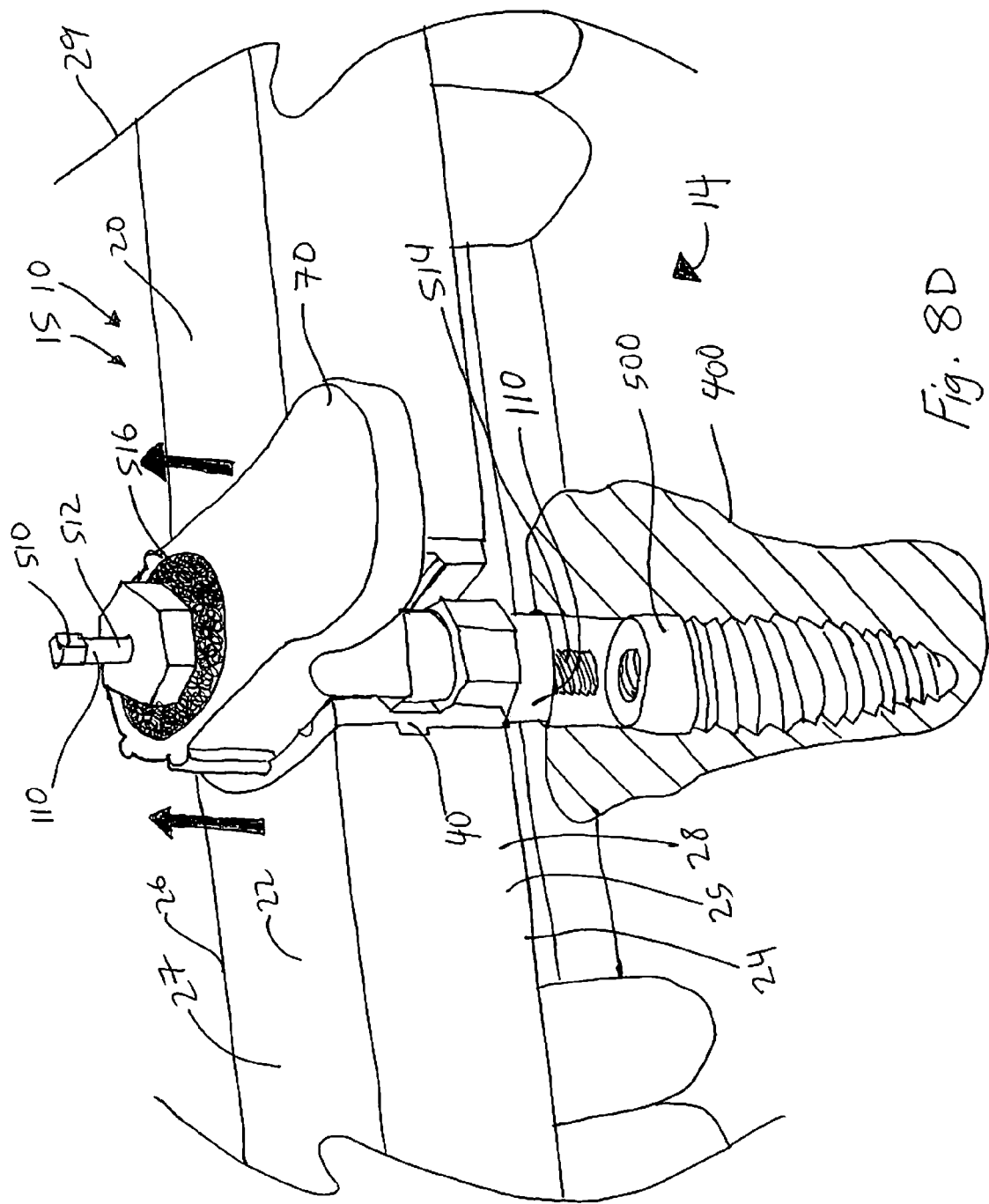
Figure 8E:
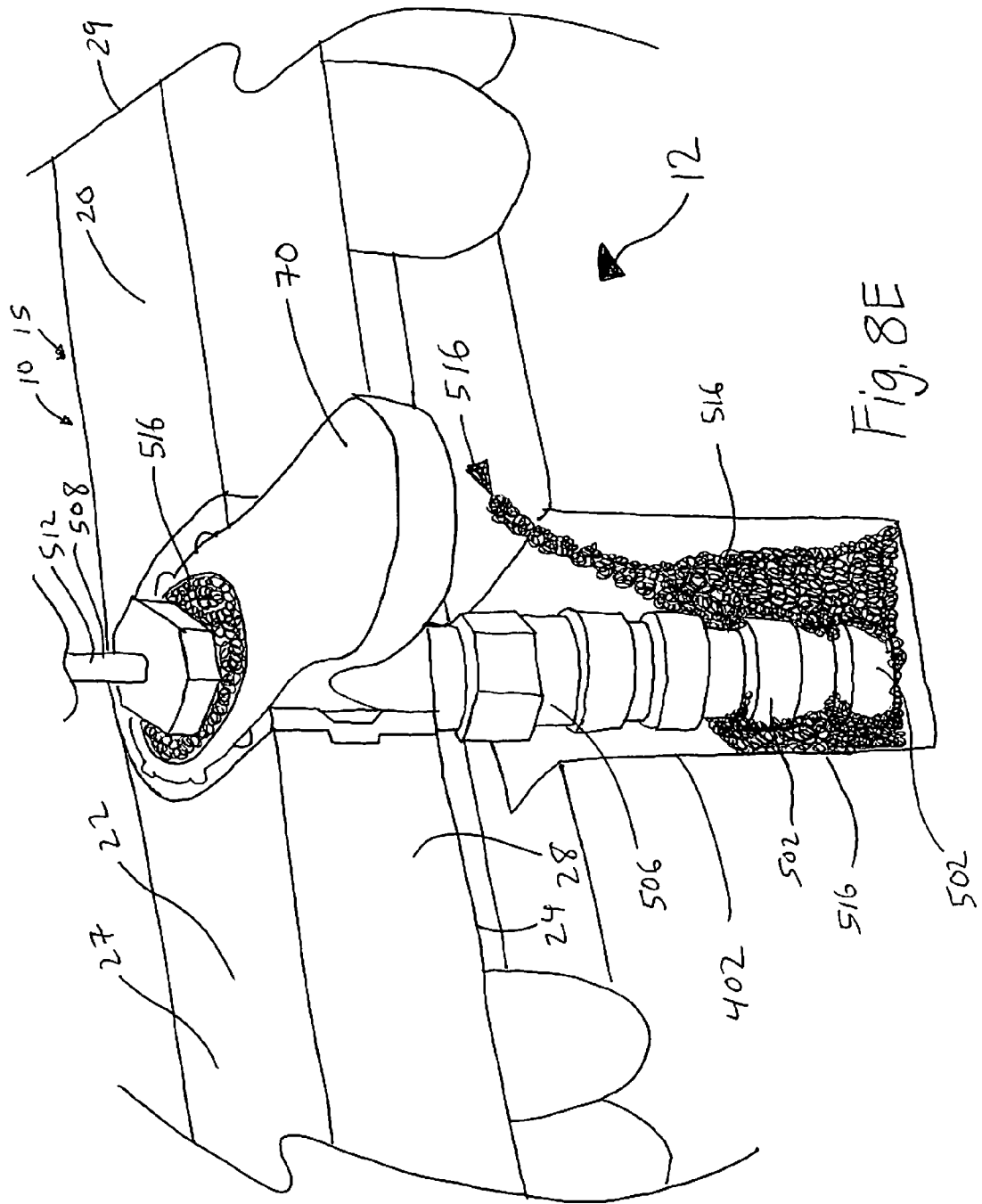
Figure 8F:
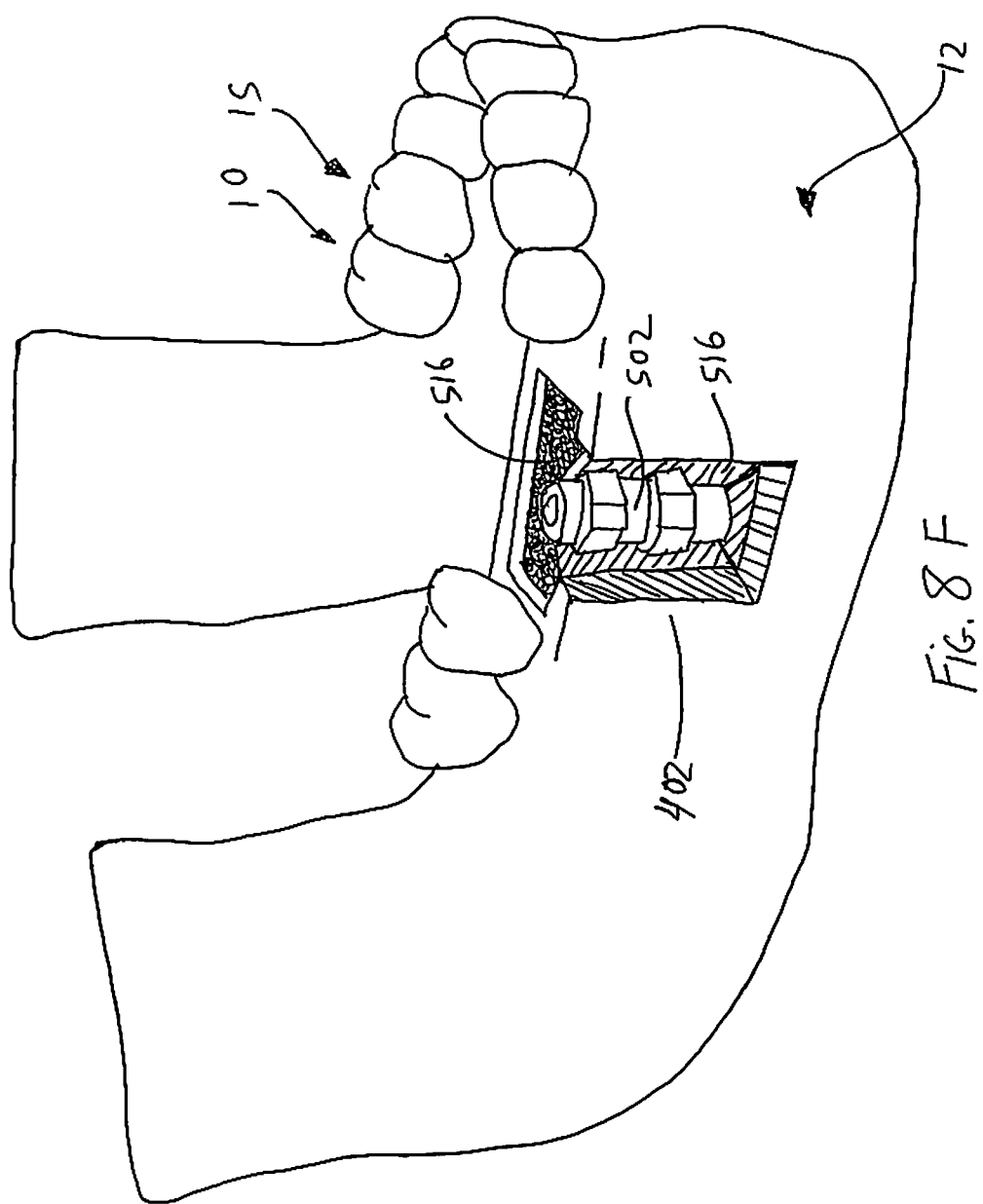

As substantially shown in FIG. 7, one possible embodiment could be a process or method 300 of use of the dental surgical guide with a tool head that can be loaded with implant appliances. The first step could step 302, affixing dental surgical guide. Here, the side-loading dental surgical guide has been created using wide variety of datum data that was acquired through mapping the patient's mouth with CT-scanning, laser scanning, dental impressions, dental casts and the like. This data can then be fully integrated by specialized software to produce a virtual model of the patient's mouth. This virtual model can then be used to develop the dental implant surgical strategy. Further, the virtual model through computer-based manufacturing processes can create the side-loading dental surgical guide that incorporates the surgical plan's positioning and operation of the dental implant appliances/(e.g., as well as the precision placement of the subject implant.) These same processes could also be used to make a translucent model of the patient's mouth showing the proposed implant site and significant structures of the mouth as they interrelate with the proposed implant surgical plan. The dental surgical guide could also be placed upon the translucent model to carry out real life modeling of the implant surgical plan; make adjustments to dental implant plan (by making changes to the operational scope/movement of one or more dental implant appliances as to be used in the surgery and the like); and carry out portions of the implant surgical plan outside of the patient's mouth (such as the creation of abutments).

The operator (e.g., dental health care professional) could then take the side-loading dental surgical guide and place it in the patient's mouth (or in the alternative, place it on the translucent model) so that the operative portion of the dental surgical guide is located proximate appropriately to proposed implant operation site/modeled implant operation site. After checking to ensure a good fit and correlation between the dental surgical guide and the patient's mouth (or the translucent model) and, the process 300 could substantially move onto next step 304, selecting the implant appliance.

In step 304, selecting the dental appliance, the operator selects the dental implant appliance for implementing, in regards to the patient, the appropriate stage of surgical plan. For instance, in the initial preparation of the implant site, the tissue cutter implant appliance may be selected. The tissue cutter is then appropriately inserted into its respective tooling head.

The tooling head if so desired could be reversibly attached to the handle using the above-described tooling head-handle means (e.g., moving the tabs of the tooling head over the respective prongs of the handle until the prong dimples "click" into the respective tab apertures). Otherwise the tooling head may be directly manipulated by the operator without the handle.

As step 304 is substantially completed, the process 300 could proceed onto step 306, insertion into the open-sided master grommet In step 306, insertion into the open-sided master grommet, the operator could in at least one embodiment, insert the tooling head through the side opening of the respective open-sided master grommet (either directly by hand or indirectly through the use of the reversibly attached handle). During such insertion, as the tooling head locking means could be fully engaged (e.g. the belt moves into proper place within the grommet grove), this action could resulting in a sound such as a "click" as well as a vibration that could be transmitted and understood by the operator that the tooling head has fully and correctly engaged/inserted and locked into its respective master grommet. Conversely, if such audible/tactile notification did not issue, the operator could understand that the tooling head was not properly inserted into its respective open-sided master grommet In at least one embodiment, wherein the tooling head is generally correctly loaded into its open-sided master grommet through the top aperture rather than the side opening of the master grommet (e.g., for handling the implant thread cutter or the implant placement tool.) In such an embodiment, the tooling head locating means may be forgone in place of the use of tooling head depth locking means. For such an insertion, the tooling head vertical ridges can be aligned up with and inserted (e.g., dropped) into the open-sided master grommet's vertical grooves. When the vertical ridges bottomed out on the vertical grooves, the tooling head has reached its appropriate operation depth and orientation within the respective master grommet Once the tooling head is properly inserted into its respective master grommet, the process 300 could generally proceed to step 308, operation of dental implant appliance. In this step 308, the operator applies either the air power tool/manual ratchet or other suitable powered means to rotate the dental implant appliance within the tooling head. For those applications, not requiring absolute depth and degree rotation precision (e.g., the tissue cutter), then the air power tool could be attached to the suitably receptive top end of the dental implant appliance to rotate the implant appliance until its collar came to rest down upon the top of the tooling head/master grommet In those dental appliances requiring additional precision (e.g., up to 1/100,000 of an inch) in their operation/movement (operation depth, final degree of rotation relative to the dental surgical guide/implant surgical site, etc.) their collars could be edged to form corners that bear tabs that could precisely engage ring of dimples created by the combined tooling head/ master grommet depressions when the dental implant appliance had descended to a specifically engineered depth/to a specific degree of rotation to stop further movement of the dental implant appliance.

In such operations, much of the rotation of the dental appliance could be provided by the air drill. As the dental implant appliance collar approaches the top of the master grommet/tooling head, the air power tool could de removed from the appliance top end and could be replaced by the manual ratchet to operate the dental implant down to its final movement/completed operational position.

As the tabs slip across the top of the master grommet/ tooling head and into their end position into their respective dimples, this action precisely stops the movement of the dental implant appliance and could further create the vibration(s) which could be the source for the audible notification ("click" sound) and the tactile notification for the dental implant appliance notification means. The issuance of such notification indicating that the dental implant appliance (e.g., implant) has reached proper operation status relative to the implant surgical site/modeled implant surgical site. The location of the tabs within the dimples could also provide a visual conformation of proper lockup of the dental implant appliance at the proper pre-set operation status.

Upon the general completion of step 308, the process 300 could substantially proceed to step 310, removal of dental implant appliance. In this step, the process of step 306 could be reversed by turning/rotating (generally counterclockwise if the dental implant appliance was involved in operations having a threaded aperture/channel in the implant surgical site/modeled implant surgical site) the dental implant appliance and lifting/clearing the operation end of the dental implant appliance up away from the top of the implant surgical site/modeled implant surgical site. Once the operation end is so cleared, the tooling head can be removed from its respective master grommet generally by reversing procedure of step 206. In this manner, the dental implant appliance and its respective tooling head is removed from the dental surgical guide.

Upon the substantial completion of step 310, the process 300 could substantially proceed back to step 304 selection of dental implant appliance to continue using appropriate dental implant appliances to carry out specific tasks of the implant surgical plan for the placement of the implant, creation of the abutment/extension and placement of the prosthetic upon the abutment/extension. It should be noted that one portion of the surgical implant plan could be completed and the side-loading dental surgical guide be placed upon the translucent model for the completion next portion of the surgical plan generally following the above-described procedure. use of the dental surgical guide) to complete various implant procedures outside of the patient's mouth. The out-of-mouth procedures afforded by the invention could include abutment formation, crown-implant fit, crown alteration, and the like.

As substantially shown in FIGS. 8A to 8F, one version of the above method 400 could provide for the adjustment or correction to the surgical plan for various in vitro changes the dental health care professional makes during the dental implant operation. Such an in-vitro change could occur when the dental healthcare professional, after initially setting the implant 500 via the surgical guide 20 in the patient's mouth 14, decides that the implant 500 is not firmly embedded in the bone mass. At that time, the dental health care professional could proceed to take those steps to remove the dental surgical guide 20 from the patient's mouth 12 and then further drive (i.e., ratchet down) the implant 500 into the bone mass or otherwise change the position, orientation, depth of the implant 500 outside the parameters originally set forth in the dental surgery plan.

At this point, the dental healthcare professional has generally deviated from the surgical plan and now significant portion of the processed planning data (for that particular implant 500 at least) may no directly longer correlate to the actual implant placement and orientation as actually placed by the dental healthcare professional in the patient's mouth. To at least partially incorporate this change into the surgical plan, the invention 10 can allow the dental healthcare professional to place an implant analogue 502 in the translucent 3D model 12 that precisely and accurately replicates in a model 12 the actual placement and orientation of the implant 500 in the patient's mouth 14.

To accomplish this objective, the dental healthcare professional places the surgical guide 20 back into the patient's mouth 14. The professional then could insert an indexing tab tooling head 504 (e.g., a index/seating jig which could also accommodate at least a portion of an indexing abutment 506) into the respective master grommet 40 to substantially locate the indexing abutment 506 (once the indexing abutment 506 placed into the indexing tab tooling head 504) proximate to the top of the placed implant 500.

The indexing abutment 506 may feature a reversible attachment means 508 for fixing itself onto the implant 500/ implant analogue 502. This attachment means 508 could include a shaft-like fastener portion having a ratchet end 512 and threaded end 514, the fastener portion 510 may movably rotate within a lengthwise shaft along the central axis of the indexing abutment 506. The fastener portion 510 could substantially present its threaded end 514 at the bottom of the indexing abutment 506 while a ratchet end 512 could be located proximate to the top of indexing abutment 506. The placement of indexing abutment 506 into indexing tab tooling head 504 as held by the dental surgical guide 20 (e.g., in the respective master grommet) generally allows the bottom of the indexing abutment 506 to come proximate to the top of the implant 500 (the implant 500 having a corresponding portion at its top for reversibly receiving the threaded end 514). By rotating the ratchet portion 512, the threaded end 514 may be driven into the top of the implant 500 to reversibly affix the indexing abutment 506 securely to the top of the implant 500.

Dental casting material 516 (e.g., a polymer such as blue mousse or the like) or other suitable securing material know to those with ordinary skill in the art can then applied to the interior of the indexing tab tooling head 504 to attach the indexing abutment 506 within the indexing tab tooling head 504 relative to the connected implant 500. Once the dental casting material 516 is set and securely locates the indexing abutment 506 within the indexing tab tooling head 504, the indexing abutment 506 is released (e.g., unscrewed) from the implant 500. The dental healthcare profession can then remove the indexing tab tool head 504/indexing abutment 506 combination from the dental surgical guide 20/patient's mouth 14.

The dental surgical guide 20 can be removed from the patient's mouth 14 to be placed on the translucent 3D model 12 where an implant surgical site analogue 402 has been previously drilled out from the model 12. An appropriate implant analogue 502 is selected and then reversibly fastened (e.g., screwed) to the bottom of the combination of indexing abutment 506/indexing tab tooling head 504. At this time, the combination may be placed into the respective master grommet 40 of the dental surgical guide 20 so that the implant analogue 502 is properly and accurately placed and oriented within the implant surgical site analogue 402 of the translucent 3D model 12. In this manner, the placement of implant analogue 502 in the translucent 3D model can be used to accurately duplicate the orientation, positioning, placement and alike of its real life implant 500 counterpart as currently secured in the patient's mouth 14.

To properly secure the implant analogue 502 as it is positioned in the implant surgical site analogue 402, the dental healthcare professional can embed the appropriate portion of the implant analogue 502 in the implant surgical site analogue 402 with an appropriate dental casting material 516 (e.g., dental cement). Once the dental casting material 516 is cured, the indexing abutment 506 may be detached (e.g., unscrewed) from the secured implant analogue 502 and the combination of indexing tab tooling head 504 and indexing abutment 506 can be removed from the dental surgical guide 20/master grommet 40 and the secured implant analogue 502.

As this procedure generally transforms (e.g., amends or corrects) the translucent 3D model 12 into an accurate representation of the patent's mouth 14 with the actual placement of the respective implant(s) 500, the model 12 (utilizing the side-loading dental surgical guide 20) can be further used to in various procedures occurring outside the patient mouth 14 to complete the rest of the implant process (e.g., create an implant abutment that can be placed on the implant 500; verify and adjust as necessary the fit of the crown that will be applied to the implant, and the like.)

Conclusion

Although the description above contains many specifications, these should not be construed as limiting the scope of the invention but as merely providing illustrations of some of the presently preferred embodiments of this invention. Thus, the scope of the invention should be determined by the appended claims and their legal equivalents rather than by the examples given.

As demonstrated above, the invention provides a CT-based, side-loading dental surgical guide system and method of use that positively locks-in dental implant appliances into a dental surgical guide with a greater degree of precision and control as to the desired operating parameters for the dental appliances. The invention also substantially provides an accompanying notification system to signal the lock-in/failure of lock-in of dental appliances with respect to their desires operating parameters as well as the means to amend a surgical plan and update 3D model of the patient's mouth when the dental healthcare professional places an implant outside the original parameters/specifications of the surgical plan, many steps of this amendment taking place outside of the patient's mouth. The invention also further reduces how wide a patient must open their mouth to accommodate such surgical procedures. As such, the invention can be used to generally reduce the cost, time, complexity, and expertise needed to place an implant in a patient's mouth, and significantly improved the efficiency of implant dentistry to generally make implant dentistry more affordable to greater numbers of the population.

What is claimed is:

1. A dental surgical guide system comprising:
   (A) a body with a set of walls, a top portion, and a bottom portion and at least one open-sided channel, the open-sided channel that continuously connects an opening of one wall from the set of walls to an opening of the top portion and to an opening of the bottom portion; and
   (B) at least one master grommet, the master grommet having a hollow grommet interior that continuously connects a side opening, a top aperture and a bottom aperture;
   (C) at least one tooling head, the tooling head having a channel that opens to and connects a top and a bottom of the tooling head, the tooling head lacking a side aperture that connects to the channel, wherein a dental implant appliance enters into the channel by being loaded into the tooling head through either the top or the bottom of the tooling head, the tooling head controlling telemetry and axes of the dental implant appliance's positioning into a surgical site;
   wherein the open-sided master grommet is placed within a respective open-sided channel to allow a dental tooling head to be placed into the master grommet through the master grommet's side opening, the tooling head engaging the master grommet in a manner that prevents the tooling head from rotating within the master grommet, the master grommet in combination with the tooling head further forms a ring of dimples radially disposed around a top aperture of the tooling head; the ring of dimples acting in conjunction with a dental implant appliance movably held by the tooling head limits the operational depth and rotation of the dental implant appliance in relation to the dental surgical guide or in relation to the tooling head or in relation to an implant surgical area analogue of a model of a patient's mouth by positively locking in the dental implant appliance into the ring of dimples.

2. The dental surgical guide system of claim 1 wherein open-sided channel has a U-shaped cross section.

3. The dental surgical guide system of claim 2 wherein the master grommet has a U-shaped cross section that is reciprocal to that of the open-sided channel.

4. The dental surgical guide system of claim 1 wherein the side opening of the master grommet is proximate to and aligned with a respective opening in one of the set of walls.

5. The dental surgical guide system of claim 1 further comprising a master grommet locating means for setting the master grommet at a specific orientation and placement within the master grommet's respective open-sided channel using a groove that interlocks with a tongue.

6. The dental surgical guide system of claim 5 wherein the master grommet locating means comprises of a laterally-located, locking groove that is radially cut into the open-sided channel wall to reciprocally receive a radially disposed tongue laterally located on an exterior of the master grommet.

7. The dental surgical guide system of claim 1 wherein the master grommet further comprises of a grommet interior wall having a laterally-oriented, radially-disposed grommet groove.

8. The dental surgical guide system of claim 7 wherein the grommet groove is so constructed to reversibly receive a tooling head having a corresponding belt laterally and radially disposed on the exterior head wall of the tooling head.

9. The dental surgical guide system of claim 7 wherein the grommet interior wall further comprises of at least one longitudinally oriented vertical groove.

10. The dental surgical guide system of claim 9 wherein the longitudinally oriented vertical groove is reciprocally and reversibly received by a corresponding vertical ridge located on a tooling head when the tooling head is placed within the master grommet interior.

11. The dental surgical guide system of claim 10 wherein the construction of one or more vertical grooves and the one or more reciprocal vertical ridges controls the depth of a tooling head's location within the tooling head's respective master grommet.

12. A dental surgical guide system comprising:
(A) a side loading dental surgical guide with a set of walls, a top portion, and a bottom portion, at least one open-sided channel, and at least one open-sided master grommet with a side opening, wherein the open-sided channel continuously connects an opening of a wall from a set of walls to an opening on the top portion and an opening of the bottom portion; wherein the open-sided master grommet is so received within a respective open-sided channel so that the open-sided channel's opening of a wall matches up with the side opening of the master grommet; and
(B) a tooling head that is reversibly received within the open-sided master grommet either through a top or a side of the master grommet in a manner that prevents the tooling head from rotating within the master grommet, the tooling head further having a body with a top and bottom connected by walls, which allow a dental implant appliance to pass at least partially through the tooling head by entering the tooling head only through either the tooling head's top or the bottom, the tooling head lacking a side aperture that prevents the dental implant appliance from entering the tooling head through the side, the tooling head controlling all telemetry and axes x, y and z of the dental implant appliance's positioning relative to a patient's mouth;
wherein a dental appliance being held by the tooling head has a collar with one or more tabs, the one or more tabs can interact with a ring of dimples radially-disposed around a top aperture of the tooling head to limit the operational depth and rotation of the dental implant appliance in relation to the dental surgical guide or in relation to the tooling head or in relation to an implant surgical area analogue of a model of a patient's mouth.

13. The system of claim 12 further comprising a tooling head locking means for reversibly locating the tooling head within its respective master grommet at a controlled orientation and placement when the tooling head is loaded into the open-sided master grommet through the side opening of the master grommet.

14. The system of claim 12 further comprising a tooling head depth locking means to locate a tooling head at certain depth relative to the master grommet when the tooling head is placed into the master grommet through the side opening of the master grommet.

15. The system of claim 12 wherein the tooling head is placed into the open-sided master grommet through the side opening of the master grommet.

16. The system of claim 12 further comprising a dental implant appliance indexing means for positively interlocking a dental implant appliance relative to the dental surgical guide so as to control the depth and angle of rotation of the dental implant appliance relative to the dental surgical guide.

17. The system of claim 16 wherein the dental implant appliance indexing means issues a notification to an operator that the dental implant appliance has reached the dental implant appliance's proper depth and angle of rotation relative to its respective tooling head.

18. The system of claim 17 wherein the notification is mechanically created and is auditory.

19. The system of claim 17 wherein the notification is tactile.

20. A method of operating a side-loading dental surgical guide comprising the following steps:
(A) providing a side-loading dental surgical guide having at least one open-sided channel that at least partially encloses an open-sided master grommet, the open side of the master grommet opening upon the open side of the open-sided channel;
(B) providing a tooling head having a body with a top and a bottom connected by a set of solid walls, the body allows a dental implant appliance to enter the tooling head only through either the top or the bottom, the solid walls allow the tooling head to control all axes and telemetry of the dental implant appliance's positioning relative to a patient's mouth;
(C) moving the tooling head through the open side of the open-sided channel;
(D) preventing the tooling head from rotating within the open-sided master grommet;
(E) securing the tooling head within the master grommet; and
(F) contacting one or more tabs on a collar of a dental appliance held by the tooling head with a ring of dimples radially-disposed around a top aperture of the tooling head to provide a notification when the dental implant appliance is properly seated in relation to the tooling head and to limit the operational depth and rotation of the dental implant appliance in relation to the dental surgical guide or in relation to the tooling head or in relation to an implant surgical area analogue of a model of a patient's mouth.

21. The method of claim 20 further comprising a step of providing tooling head locking means.

22. The method of claim 21 further comprising a step of mechanically creating a notification through the locking means that the tooling head is properly located within the master grommet.

23. The method of claim 20 further comprising a step of providing a dental implant appliance that is placed with the tooling head that fits within a master grommet.

24. The method of claim 23 further comprising a step of mechanically issuing a notification when the dental implant appliance positively interlocks with the dental surgical guide at a desired depth relative to the guide.

25. The method of claim 23 further comprising a step of mechanically issuing a notification when the dental implant appliance positively interlocks with the dental surgical guide at a desired rotational degree relative to the guide.

26. The method of claim 23 further comprising a step of preventing the dental implant appliance rotation from exceeding a previously specified angle of rotation at a specified depth.

27. The method of claim 23 further comprising a step of reversibly locking the dental implant relative to the dental surgical guide when the implant has reached a desired depth and specific angle of rotation.

28. A dental implant system comprising:
(A) a dental implant guide with a set of walls, a top portion, and a bottom portion and at least one channel that can receive a master grommet;
(B) a tooling head that is received within the master grommet in a manner that prevents the tooling head from rotating within the master grommet, the tooling head having solid exterior wall and a solid interior wall, both walls allowing the tooling head to control axes and telemetry of a top-loaded dental implant appliance's positioning relative to a patient's mouth;
(C) a dental implant appliance that is movably received within at least a portion of the master grommet;
wherein the master grommet, the tooling head, and the dental implant appliance form an indexing means that locks the dental implant appliance to prevent the further rotational movement of the dental implant appliance after the dental implant appliance has obtained the desired depth and angle of final rotation with respect to either the implant surgical site or the implant surgical site analogue, the indexing means further comprising a ring of dimples radially-disposed around a top aperture of the tooling head, the ring of dimples acting in concert with one or more tabs presented by a collar of a dental appliance being held by the tooling head to create a mechanical sound or vibration.

29. The dental implant system of claim 28 wherein the indexing means further acts as a notification means to mechanically issue a sound informing an operator when the dental appliance has obtained the proper operating parameters.

30. The dental implant system of claim 29 wherein the notification means mechanically creates a vibration to inform an operator when the dental appliance has obtained the proper operating parameters.

31. The dental implant system of claim 29 wherein the notification means informs an operator by not creating a sound or vibration if the dental appliance has not obtained the proper operating parameters for either the implant surgical site or the implant surgical site analogue.

* * * * *